United States Patent [19]
Konno et al.

[11] Patent Number: 5,793,539
[45] Date of Patent: Aug. 11, 1998

[54] OPTICAL SYSTEM FOR ENDOSCOPES

[75] Inventors: Mitsujiro Konno, Hoya; Shinya Matsumoto, Machida; Toshikazu Takayama; Takayuki Suzuki, both of Hachioji; Akira Hasegawa, Akishima, all of Japan

[73] Assignee: Olympus Optical Co., Ltd., Tokyo, Japan

[21] Appl. No.: 363,812

[22] Filed: Dec. 27, 1994

[30] Foreign Application Priority Data

Dec. 27, 1993 [JP] Japan ............... 5-346918

[51] Int. Cl.$^6$ ............... G02B 13/18
[52] U.S. Cl. ............... 359/739; 359/708
[58] Field of Search ............... 359/739, 740, 359/738, 708

[56] References Cited

U.S. PATENT DOCUMENTS 4,902,115  2/1990  Takahashi ............... 359/739

FOREIGN PATENT DOCUMENTS 3732260  7/1988  Germany.
63-78119  4/1988  Japan.

Primary Examiner—Scott J. Sugarman
Attorney, Agent, or Firm—Cushman Darby & Cushman IP Group of Pillsbury Madison & Sutro LLP

[57]  ABSTRACT

An optical system for endoscopes which comprises a stop having a variable aperture and is configured so as to produce spherical aberration for preventing an image surface thereof from being shifted in a direction opposite to the object side by narrowing the aperture of the stop, whereby the optical system is free from insufficiency in brightness and degradation in resolution thereof on a side farther from the optical system within a depth of field thereof, and has another side of the depth of field brought close to the optical system.

24 Claims, 24 Drawing Sheets

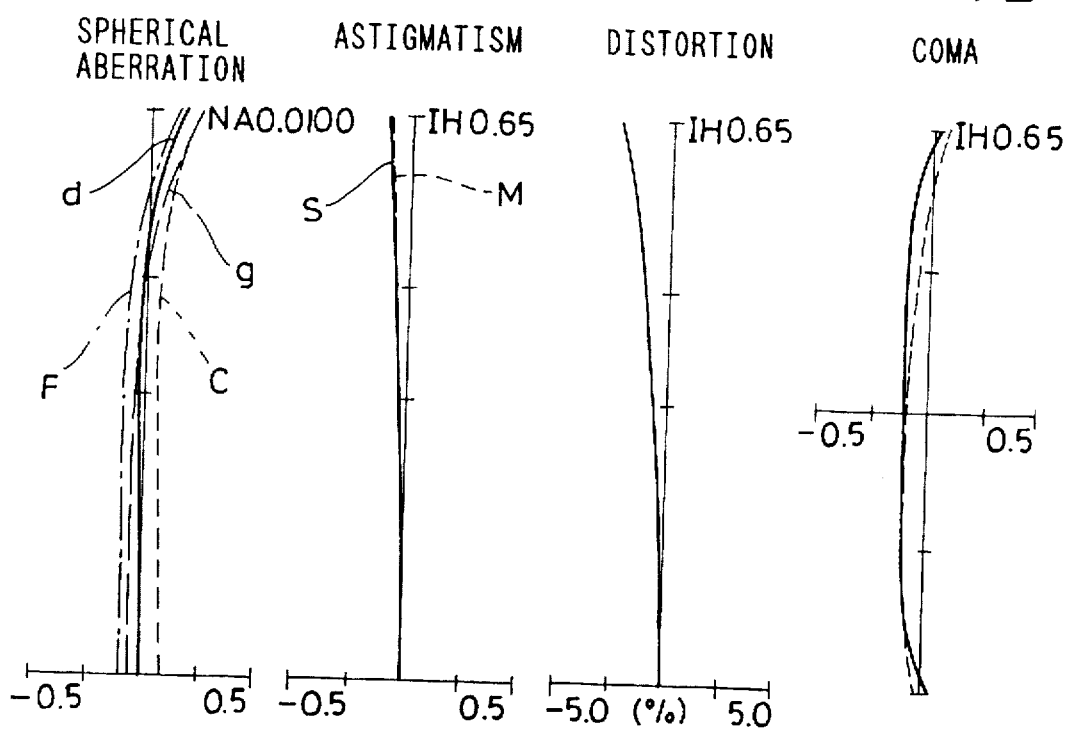
FIG. 9A SPHERICAL ABERRATION
FIG. 9B ASTIGMATISM
FIG. 9C DISTORTION
FIG. 9D COMA
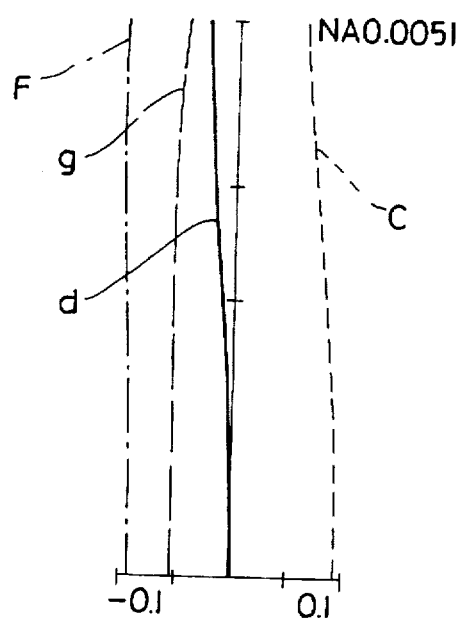
FIG. 10 SPHERICAL ABERRATION

OPTICAL SYSTEM FOR ENDOSCOPES

BACKGROUND OF THE INVENTION a) Field of the Invention

The present invention relates to an optical system equipped with a stop having a variable aperture, and more specifically to an optical system for endoscopes equipped with such a stop.

b) Description of the Prior Art

In the recent years, endoscope apparatuses have been available which consist of as illustrated in FIG. 1, a non-flexible endoscope 1 and a TV camera 2 having a built-in solid-state image pickup device 3 such as a CCD image sensor (hereinafter referred to as CCD's) attached to an eyepiece lens system of the endoscope 1 so that the endoscope apparatus permits displaying an image in a human cavity on a monitor TV 7 for medical diagnoses and treatments. In FIG. 1, the reference numeral 4 represents optical low pass filters, the reference numeral 5 designates an imaging lens system, the reference numeral 6 denotes a camera control unit, the reference numeral 8 represents an objective lens system of a non-flexible endoscope, the reference numerals 9a and 9b designate relay lens units, and the reference numeral 10 denotes an eyepiece lens system. Considering a fact that such an endoscope apparatus is used mainly for surgical operations, it is tedious to control the endoscope apparatus so as to maintain a constant range of observation by controlling a focused condition of the endoscope apparatus during a surgical operation. It is conceivable, as a means for correcting this defect, to utilize an autofocus mechanism. However, the autofocus mechanism can hardly focus the endoscope apparatus precisely on a location which a surgical operator wants to observe since he does not always want to observe a center of the visual field of the endoscope apparatus, unlike a case where he handles an ordinary photographic camera. It is therefore desirable to configure it so as to have a large depth of field for a satisfactory range of observation. FIG. 2A, FIG. 2B, FIG. 2C, FIG. 2D, FIG. 2E and FIG. 2F illustrate relations between MTF's and amount of defocus of lens systems which have favorably corrected aberrations: FIG. 2A showing an object located at a best distance, FIG. 2B showing an object located at a long distance from the lens system and FIG. 2C showing an object located at a short distance from the lens system. On a coordinates system adopted for illustrating the MTF's, the abscissa represents positions in a direction of an optical axis and the reference symbol I designates a predetermined design image surface. In FIG. 2D, FIG. 2E and FIG. 2F, MTF's obtained with apertures of stops kept fully open are traced in solid lines, whereas MTF's obtained with the apertures of the stops kept narrowed are traced in dashed lines. Since an MTF has values which dependent on spatial frequencies, the curves traced in FIG. 2D, FIG. 2E and FIG. 2F were traced at a spatial frequency suited for evaluating optical performance of optical systems (an evaluation frequency). A variation of an object point causes a shift of an image surface from the predetermined design image surface I. A depth of field by definition is a range between two points which are located near and far from respectively an optical system, and at which an MTF has a value exceeding an allowable level when an object distance varies. An MTF is improved as a whole on an image surface, or a depth of field is enlarged simply by narrowing an aperture of a stop disposed in an optical system.

For simply enlarging a depth of field, it is sufficient to narrow an aperture of a stop so as to increase an F number as described above. In case of such an endoscope apparatus as that shown in FIG. 1 which is configured so as to transmit an image a large number of times by the relay lens units or the similar means, however, the endoscope apparatus mostly produces negative spherical aberration as shown in FIG. 3A. Accordingly, this endoscope apparatus allows a peak of an MTF thereof to be shifted as shown in FIG. 3B by narrowing an aperture of a stop disposed therein, thereby causing a shift of a best image surface thereof in a direction opposite to the object side. On the coordinate system, the abscissa is traced taking as positive a direction from the object side toward an image formed by the optical system. Considering reversely taking a predetermined image receiving surface as standard, this fact means that objects located at longer distance are brought into focus by narrowing the aperture of the stop. As a result, the endoscope apparatus may have a depth of field which becomes insufficient for the objects located at the short distances, or does not permit satisfactorily observing objects located at extremely short distances when the aperture of the stop is narrowed. On the other hand, the depth of field of the endoscope apparatus tends to be increased for observing the objects located at the longer distances, but the endoscope apparatus may not permit observing these objects due to brightness which is lowered by narrowing the aperture of the stop.

The optical system disclosed by Japanese Patent Kokai Publication No. Sho 63-78,119 comprises, in the vicinity of a pupil thereof, a lens component having focal lengths which are different dependenting on NA's (numerical apertures), i.e., between a first region ($A_1$) and a second region ($A_2$), whereby the optical system prevents insufficiency in brightness by fully opening an aperture of a stop disposed therein as shown in FIG. 4A for observing objects located at long distances and shifts a paraxial image surface toward the object side by narrowing the aperture of the stop as shown in FIG. 4B for observing objects located at short distances so that these objects are brought into focus on the image surface, or a depth of field thereof is broadened toward the objects located at the short distances. When this optical system is used in the endoscope apparatus illustrated in FIG. 1 which is configured so as to transmit an image a large number of times by the relay lens units, however, the endoscope apparatus will produce negative spherical aberration as shown in FIG. 5A.

The lens component which consists of the first region $A_1$ and the second region $A_2$ having focal lengths different from each other has Gaussian images surfaces of the two regions respectively. In FIG. 5A and FIG. 5B, the reference symbol $G_1$ represents a Gaussian image surface of the first region $A_1$ and the reference symbol $G_2$ designates a Gaussian image surface of the second region $A_2$. Further, the abscissa is taken along a direction of an optical axis, the ordinate represents numerical apertures and the reference symbol MS designates a spherical aberration curve. Illustrated in FIG. 5B is a condition of rays which are condensed in the vicinities of the image surfaces by the optical system. Since the optical system condenses rays which have different heights on the lens component onto the separate Gaussian image surfaces as shown in FIG. 4B, the optical system focuses rays onto two points while an aperture of a stop disposed therein is kept fully open. Accordingly, the optical system cannot have a high resolving power due to a fact that a light bundle passing therethrough has a certain extent of spreading on the optical axis at any location in the direction of the optical axis obtained by narrowing the aperture of the stop from a numerical aperture of $NA_M$. In FIG. 5A, the reference symbol NA represents a numerical aperture obtained by fully opening the aperture of the stop, and the reference symbol $NA_B$ designates a numerical aperture corresponding to a border between the first region $A_1$ and the second region $A_2$. Further, the resolving power of this optical system can be enhanced by using a stop which is switchable for selection between a condition where the stop allows transmission therethrough only of rays having passed through the first region $A_1$ and another condition where it allows transmission therethrough only of rays having passed through the second region $A_2$. When such a stop is used in the optical system, however, the stop results in an abrupt change of brightness in two steps, thereby producing a defect that the optical system is rather inconvenient for practical use due to the abrupt change in brightness. In addition, the optical system cannot provide, in practical use, brightness which is sufficient for observing the objects located at the long distances.

SUMMARY OF THE INVENTION

A primary object of the present invention is to provide an endoscope apparatus equipped with an optical system which is configured so as to be free from insufficient brightness for objects located at long distances, does not permit degradation of resolving power thereof and has a depth of field improved for observing objects located at short distances.

For accomplishing the object described above, the optical system for endoscopes according to the present invention comprises a stop means having a variable aperture and is configured so as to permit controlling aberrations, spherical aberration in particular, in the optical system as a whole so that an image surface of the optical system is not shifted in a direction opposite to a direction toward the object side by narrowing the aperture of the stop means.

The optical system according to the present invention is configured so as to produce substantially no spherical aberration or positive spherical aberration, for example, in the optical system as a whole, thereby allowing substantially no shift of an image surface thereof or a shift of the image surface only in the direction toward the object side.

The optical system according to the present invention adopts an aspherical surface as a means for almost zeroing or making positive spherical aberration in an ordinary optical system. By using an aspherical surface which has a substantially planar reference sphere, it is possible to almost zero or make positive spherical aberration with no influence on the other aberrations.

The optical system for endoscopes according to the present invention comprises relay lens units for transmitting an image of an object to a predetermined location, an optical element producing positive spherical aberration which is disposed at a location of a pupil of the optical system or in the vicinity thereof, and a stop means which is capable of varying a shape and a size of an aperture formed therein; and is configured so as to always provide an appropriate range of observation by fully opening the aperture of the stop means for observing or photographing object located at long distances and by narrowing the aperture of the stop means for observing or photographing objects located at short distances.

Generally speaking, optical systems which comprise relay lens systems produce remarkably negative spherical aberration. It is therefore possible to accomplish the above-mentioned object by disposing an optical element producing positive spherical aberration, for example, an optical element having at least one aspherical surface producing positive spherical aberration, in an optical system so that spherical aberration is almost zeroed or made positive in the optical system as a whole.

An optical system for endoscopes which can accomplish the object of the present invention can be obtained by disposing the optical element producing positive spherical aberration in an external TV camera for endoscopes so that the TV camera can be selectively combined with different types of endoscopes.

A non-flexible endoscope has such a configuration as that shown in FIG. 1, for example, and comprises an optical system which generally produces negative spherical aberration. When an aperture of a stop S is narrowed as shown in FIG. 6B from a condition shown in FIG. 6A wherein the stop is fully open, a best focus position $B_f$ of the optical system is shifted from the location shown in FIG. 6A to another location shown in FIG. 6B. Therefore, a depth of field of the optical system can scarcely be improved for the objects located at short distances by narrowing the aperture of the stop. An effect for improving a depth of field for the object located at the short distances can be imparted to an optical system which produces negative spherical aberration by disposing the optical element producing positive spherical aberration in the optical system so as to shift the negative spherical aberration for a distance as long as possible in the positive direction. For this purpose, it desirable to dispose the optical element producing the positive spherical aberration at a location as close as possible to a pupil of the optical system. That is to say, it is possible, by disposing the optical element in the vicinity of the pupil of the optical system, to shift spherical aberration as desired for the optical system according to the present invention, with little influences on the other aberrations. In addition, it is possible to use an aspherical lens component or the similar member as the optical element producing positive spherical aberration.

Speaking of an optical system wherein spherical aberration is overcorrected as shown in FIG. 7A, for example, a best image surface of the optical system is shifted toward the object side as shown in FIG. 7B when spherical aberration at a location of a pupil thereof is shifted in a direction indicated by an arrow by narrowing an aperture of a stop disposed therein. In FIG. 7B, a curve traced in a solid line indicates an MTF which is obtained by fully opening the aperture of the stop and another curve traced in a dashed line indicates another MTF which is obtained by narrowing the aperture of the stop.

As is understood from the foregoing description, the endoscope apparatus according to the present invention is also characterized in that it comprises an optical system which is configured so as to overcorrect spherical aberration as well as a stop mechanism which varies a shape and a size of an aperture formed in a stop.

BRIEF DESCRIPTION OF THE DRAWINGS

FIG. 9A through FIG. 9D show graphs illustrating aberration characteristics of the first embodiment of the present invention;

FIG. 10 shows a graph illustrating spherical aberration within a narrow NA region of the first embodiment of the present invention;

DETAILED DESCRIPTION OF THE PREFERRED EMBODIMENTS

Figure 1:
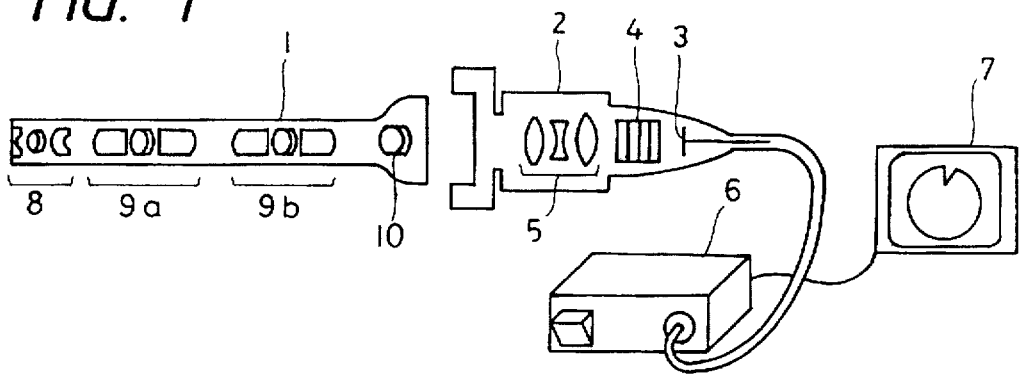
FIG. 1 shows a sectional view illustrating a configuration of an endoscope apparatus which comprises a non-flexible endoscope.
Figure 2A:
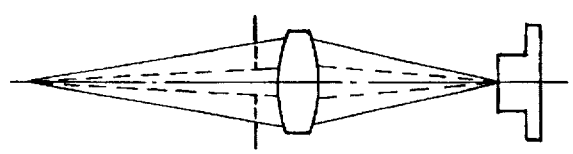
FIG. 2A, FIG. 2B, FIG. 2C, FIG. 2D, FIG. 2E and FIG. 2F show diagrams illustrating relations between imaging points and MTF's of lens components which have corrected aberrations.
Figure 2D:
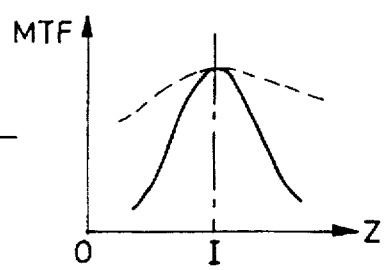
Figure 2B:
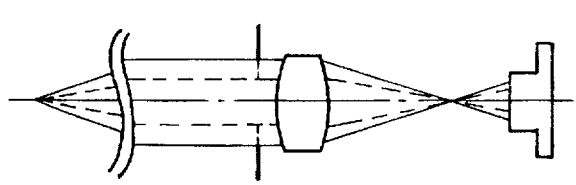
Figure 2E:
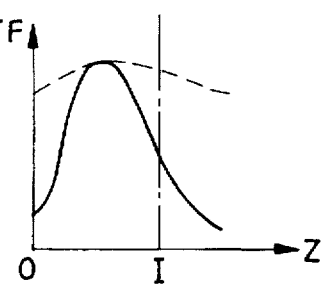
Figure 2C:
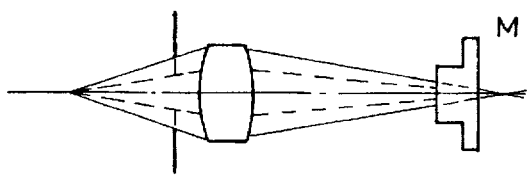
Figure 2F:
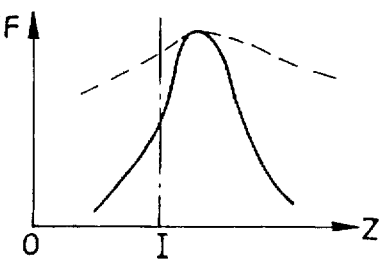
Figure 3A:
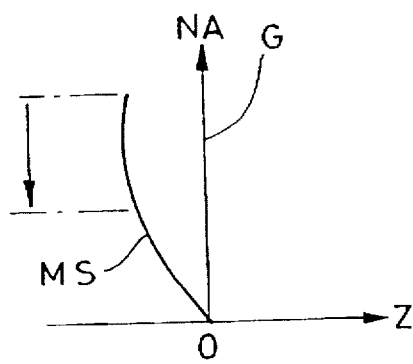
FIG. 3A and FIG. 3B show graphs illustrating negative spherical aberration and an MTF.
Figure 3B:
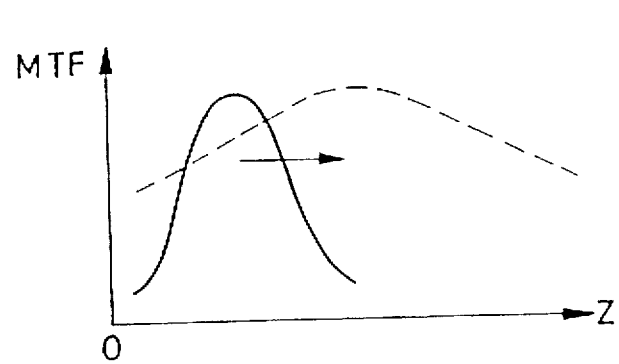
Figure 4A:
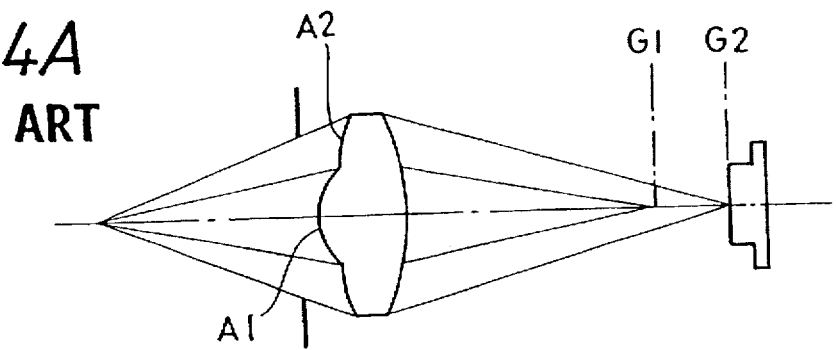
FIG. 4A and FIG. 4B show sectional views illustrating a composition of a conventional lens system which is configured so as to have a depth of field widened toward an object located at a short distance.
Figure 4B:
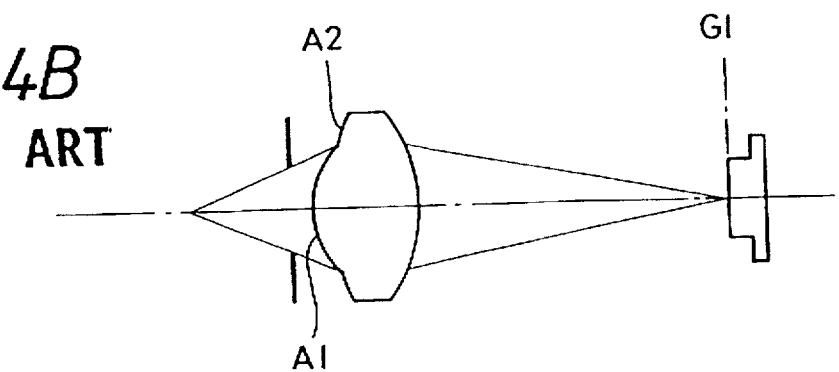
Figure 5A:
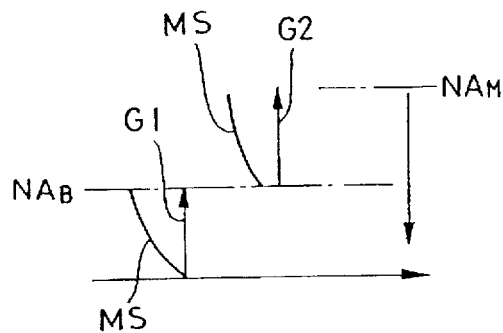
FIG. 5A and FIG. 5B show diagrams illustrating spherical aberration and MTF's of the lens system shown in FIG. 4A and FIG. 4B.
Figure 5B:
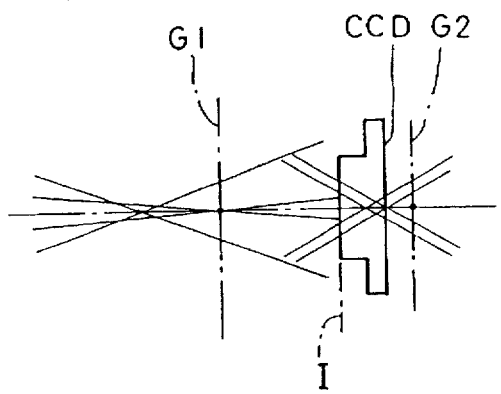
Figure 7A:
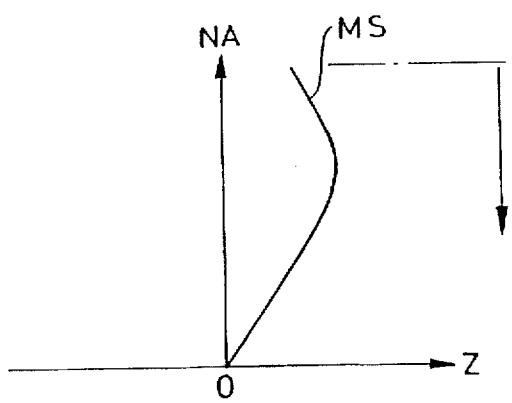
FIG. 7A and FIG. 7B show graphs illustrating a relationship among a location of a stop, a position of a best image surface and an MTF of a lens system which produces positive spherical aberration.
Figure 7B:
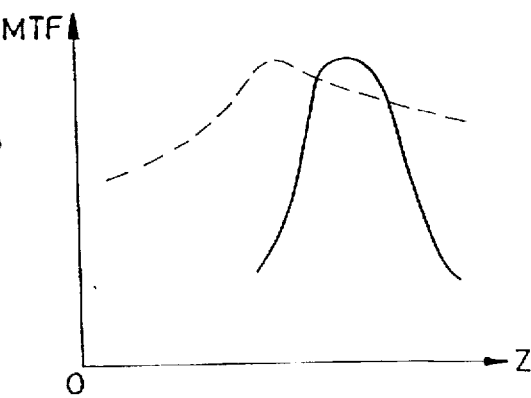
Figure 6A:
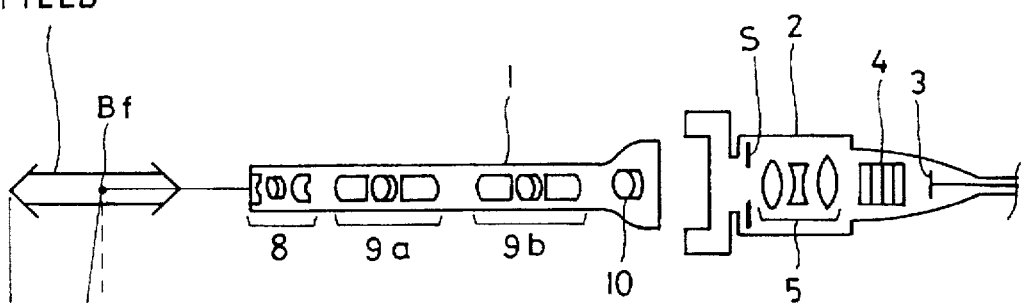
FIG. 6A and FIG. 6B show sectional views illustrating a location of a stop disposed in an optical system for endoscopes and best focus positions thereof.
Figure 6B:
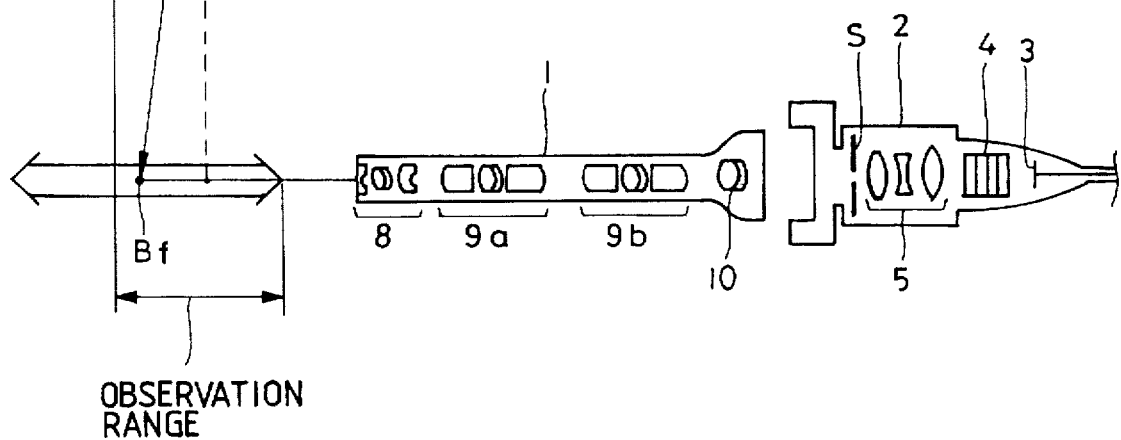

Now, the endoscope apparatus according to the present invention will be described in more detail below with reference to the preferred embodiments thereof illustrated in the accompanying drawings. A first embodiment of the optical system to be used in the endoscope apparatus according to the present invention has a composition illustrated in FIG. 8 and the numerical data listed below:

Embodiment 1
f = 1.000, F number = 19.131, image height = 0.6550

$r_1 = \infty$
$\quad d_1 = 0.1118 \qquad n_1 = 1.76900 \qquad v_1 = 64.15$
$r_2 = \infty$
$\quad d_2 = 0.0319$
$r_3 = 2.6462$ (aspherical surface)
$\quad d_3 = 0.2077 \qquad n_2 = 1.78472 \qquad v_2 = 25.71$
$r_4 = \infty$
$\quad d_4 = 0.0639 \qquad n_3 = 1.58144 \qquad v_3 = 40.75$
$r_5 = 0.1917$
$\quad d_5 = 0.1278$
$r_6 = \infty$
$\quad d_6 = 0.4095 \qquad n_4 = 1.80610 \qquad v_4 = 40.95$
$r_7 = \infty$(aperture stop)
$\quad d_7 = 1.0857 \qquad n_5 = 1.80610 \qquad v_5 = 40.95$
$r_8 = -0.6903$
$\quad d_8 = 0.0479$
$r_9 = 1.3246$
$\quad d_9 = 0.4792 \qquad n_6 = 1.60311 \qquad v_6 = 60.70$
$r_{10} = -0.5042$
$\quad d_{10} = 0.1597 \qquad n_7 = 1.84666 \qquad v_7 = 23.88$
$r_{11} = -2.2115$ -continued

| | | |
|---|---|---|
| $d_{11} = 0.4521$ | | |
| $r_{12} = -0.4345$ | | |
| $d_{12} = 0.1597$ | $n_8 = 1.58144$ | $v_8 = 40.75$ |
| $r_{13} = \infty$ | | |
| $d_{13} = 0.3674$ | $n_9 = 1.60311$ | $v_9 = 60.70$ |
| $r_{14} = -0.6363$ | | |
| $d_{14} = 1.1182$ | | |
| $r_{15} = 3.0238$ | | |
| $d_{15} = 6.9808$ | $n_{10} = 1.62004$ | $v_{10} = 36.25$ |
| $r_{16} = \infty$ | | |
| $d_{16} = 0.4121$ | | |
| $r_{17} = 2.2567$ | | |
| $d_{17} = 0.1597$ | $n_{11} = 1.80610$ | $v_{11} = 40.95$ |
| $r_{18} = 1.0310$ | | |
| $d_{18} = 0.4792$ | $n_{12} = 1.65160$ | $v_{12} = 58.52$ |
| $r_{19} = -4.0382$ | | |
| $d_{19} = 0.2875$ | | |
| $r_{20} = \infty$ | | |
| $d_{20} = 6.9808$ | $n_{13} = 1.62004$ | $v_{13} = 36.25$ |
| $r_{21} = -3.0238$ | | |
| $d_{21} = 1.2780$ | | |
| $r_{22} = 3.0238$ | | |
| $d_{22} = 6.9808$ | $n_{14} = 1.62004$ | $v_{14} = 36.25$ |
| $r_{23} = \infty$ | | |
| $d_{23} = 0.4121$ | | |
| $r_{24} = 2.2567$ | | |
| $d_{24} = 0.1597$ | $n_{15} = 1.80610$ | $v_{15} = 40.95$ |
| $r_{25} = 1.0310$ | | |
| $d_{25} = 0.4792$ | $n_{16} = 1.65160$ | $v_{16} = 58.52$ |
| $r_{26} = -4.0382$ | | |
| $d_{26} = 0.2875$ | | |
| $r_{27} = \infty$ | | |
| $d_{27} = 6.9808$ | $n_{17} = 1.62004$ | $v_{17} = 36.25$ |
| $r_{28} = -3.0238$ | | |
| $d_{28} = 1.2780$ | | |
| $r_{29} = 3.0238$ | | |
| $d_{29} = 6.9808$ | $n_{18} = 1.62004$ | $v_{18} = 36.25$ |
| $r_{30} = \infty$ | | |
| $d_{30} = 0.4121$ | | |
| $r_{31} = 2.2567$ | | |
| $d_{31} = 0.1597$ | $n_{19} = 1.80610$ | $v_{19} = 40.95$ |
| $r_{32} = 1.0310$ | | |
| $d_{32} = 0.4792$ | $n_{20} = 1.65160$ | $v_{20} = 58.52$ |
| $r_{33} = -4.0382$ | | |
| $d_{33} = 0.2875$ | | |
| $r_{34} = \infty$ | | |
| $d_{34} = 6.9808$ | $n_{21} = 1.62004$ | $v_{21} = 36.25$ |
| $r_{35} = -2.2567$ | | |
| $d_{35} = 3.1214$ | | |
| $r_{36} = 3.3895$ | | |
| $d_{36} = 0.1438$ | $n_{22} = 1.78472$ | $v_{22} = 25.71$ |
| $r_{37} = 1.3059$ | | |
| $d_{37} = 0.4153$ | $n_{23} = 1.66672$ | $v_{23} = 48.32$ |
| $r_{38} = -3.0026$ | | |
| $d_{38} = 0.5415$ | | |
| $r_{39} = \infty$ | | |
| $d_{39} = 0.4792$ | $n_{24} = 1.76820$ | $v_{24} = 71.79$ |
| $r_{40} = \infty$ | | |
| $d_{40} = 0.5112$ | | |
| $r_{41} = \infty$ | | |
| $d_{41} = 1.1540$ | $n_{25} = 1.76820$ | $v_{25} = 71.79$ |
| $r_{42} = \infty$ | | |
| $d_{42} = 0.1597$ | $n_{26} = 1.51633$ | $v_{26} = 64.15$ |
| $r_{43} = \infty$(aspherical surface) | | |
| $d_{43} = 0$ | | |
| $r_{44} = \infty$(aperture stop) | | |
| $d_{44} = 1.9968$ | | |
| $r_{45} = 1.5974$ | | |
| $d_{45} = 0.6663$ | $n_{27} = 1.81600$ | $v_{27} = 46.62$ |
| $r_{46} = 6.9371$ | | |
| $d_{46} = 0.4275$ | | |
| $r_{47} = -4.3812$ | | |
| $d_{47} = 0.4639$ | $n_{28} = 1.74077$ | $v_{28} = 27.79$ |
| $r_{48} = 1.0667$ | | |
| $d_{48} = 0.5329$ | | |
| $r_{49} = 2.3230$ | | |
| $d_{49} = 0.5469$ | $n_{29} = 1.67003$ | $v_{29} = 47.25$ |
| $r_{50} = -4.1071$ | | |
| $d_{50} = 0.7987$ | | |
| $r_{51} = \infty$ | | |
| $d_{51} = 0.1597$ | $n_{30} = 1.51633$ | $v_{30} = 64.15$ |
| $r_{52} = \infty$ | | | aspherical surface coefficients
(3rd surface)  $P = 1$, $E = 0.14239 \times 10$,  $F = -0.35843 \times 10$
(43th surface)  $P = 1$, $E = 0.58421 \times 10^{-1}$,  $F = 0.10833 \times 10^{-4}$ wherein the reference symbols $r_1, r_2, \ldots$ represent radii of curvature on surfaces of respective lens elements, the reference symbols $d_1, d_2, \ldots$ designate thicknesses of the respective lens elements and air-spaces reserved therebetween, the reference symbols $n_1, n_2, \ldots$ denote refractive indices of the respective lens elements, and the reference symbols $v_1, v_2, \ldots$ represent Abbe's numbers of the respective lens elements.

Further, the aspherical surface mentioned in the numerical data listed above has a shape expressed by the following formula:

$$Sag = (h^2/r)/\sqrt{1 + (1 - p(h/r)^2)} + Eh^4 + Fh^6 + \ldots$$

wherein the reference symbol h represents a height of a ray passing through the aspherical surface, the reference symbol Sag designates a value, in a direction along an optical axis on a coordinates system, of a point at a height of h on the aspherical surface (on an assumption that Sag has a value of 0 when h is equal to 0), the reference symbol r designates a radius of curvature on a portion of the aspherical surface located on the optical axis (a radius of curvature on a reference sphere of the aspherical surface), and the reference symbols p, E, F, . . . denote aspherical surface coefficients.

Figure 8:
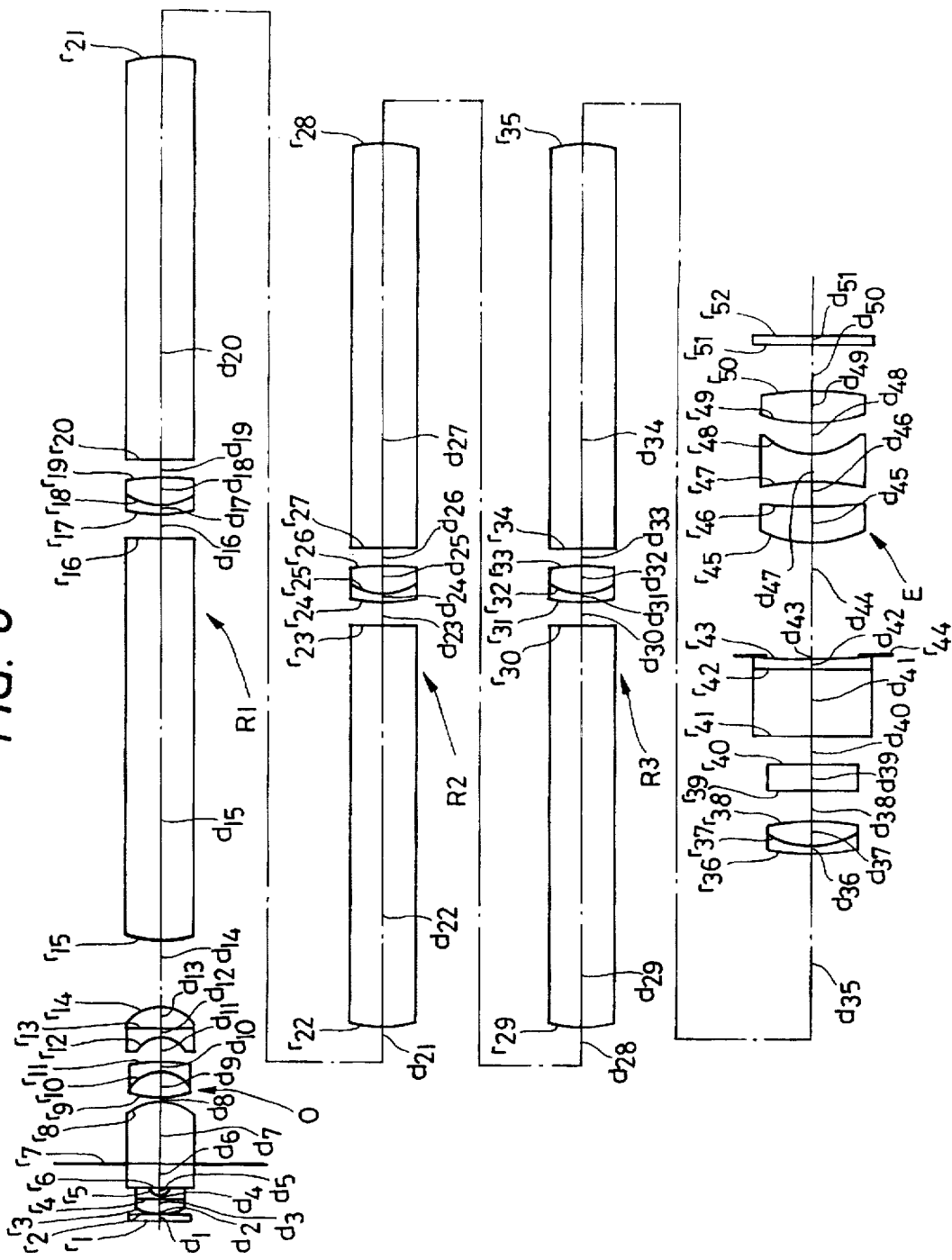
FIG. 8 shows a sectional view illustrating a composition of a first embodiment of the optical system for endoscopes according to the present invention.

The first embodiment described above has a composition wherein an aspherical lens component (an optical element obtained by transforming a surface of a plane parallel plate into an aspherical surface) is disposed in the vicinity of an eye point of an optical system for non-flexible endoscopes which is generally used and has favorably corrected aberrations so that the optical system as a whole produces spherical aberration in the positive direction, or the optical system as a whole overcorrects spherical aberration due to the positive spherical aberration produced by the aspherical lens component. That is to say, a surface $r_{43}$ disposed in the first embodiment functions as the aspherical surface which serves for allowing the optical system as a whole to produce spherical aberration in the positive direction. In FIG. 8, the reference symbol O represents an objective lens system, the reference symbols $R_1$, $R_2$ and $R_3$ designate relay lens units, the reference symbol E denotes an eyepiece lens system, and the reference symbol A represents an adaptor lens system.

Figure 11A:
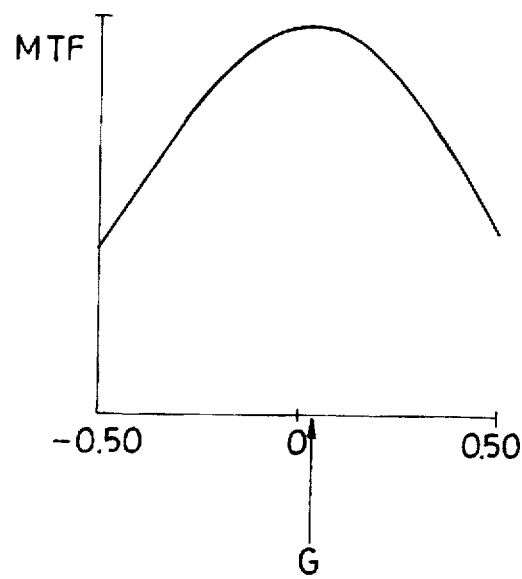
FIG. 11A and FIG. 11B show graphs illustrating MTF's of the first embodiment of the present invention.
Figure 11B:
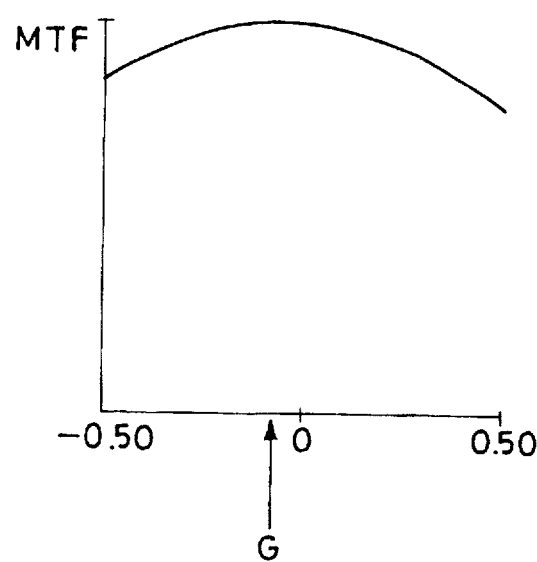
Figures 12A, 12B, 12C, 12D:
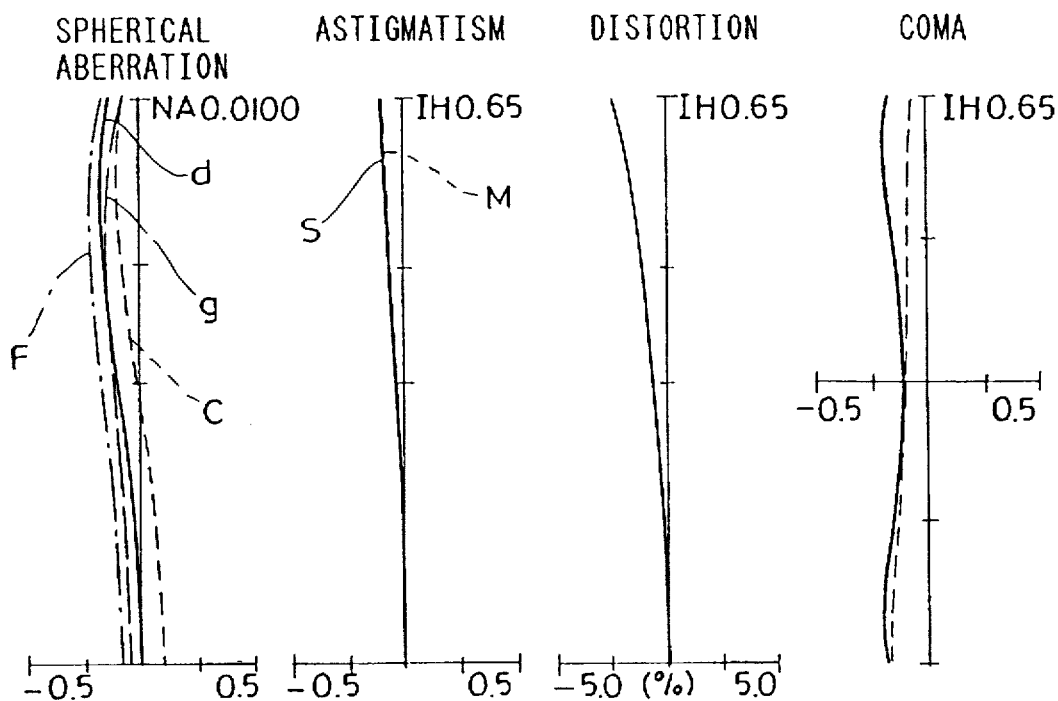
FIG. 12A through FIG. 12D show curves illustrating aberration characteristics of a conventional optical system for endoscopes.

The first embodiment has aberration characteristics illustrated in FIG. 9A, FIG. 9B, FIG. 9C and FIG. 9D and when it is set at an NA of 0.0051, it produces spherical aberration shown in FIG. 10. The first embodiment has MTF's which are illustrated in FIG. 11A and FIG. 11B.

Figure 13:
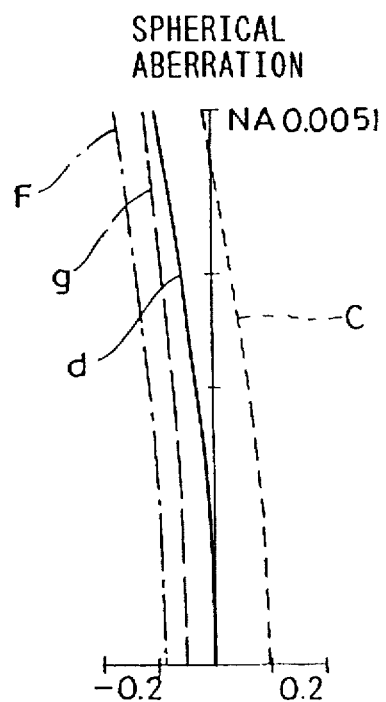
FIG. 13 shows a curve illustrating spherical aberration within a narrow NA region of the conventional optical system for endoscopes.

FIG. 12A, FIG. 12B, FIG. 12c and FIG. 12D illustrate aberration characteristics of a conventional optical system for non-flexible endoscopes having a composition which is similar to that of the first embodiment of the present invention but does not comprise an aspherical surface in the vicinity of an eye point thereof, or uses a planar surface in place of the aspherical surface $r_{43}$. FIG. 13 visualizes spherical aberration produced by this conventional optical system for endoscopes when it is set so as to have an NA of 0.0051. Further, this conventional example has MTF's shown in FIG. 14A and FIG. 14B.

Figure 14A:
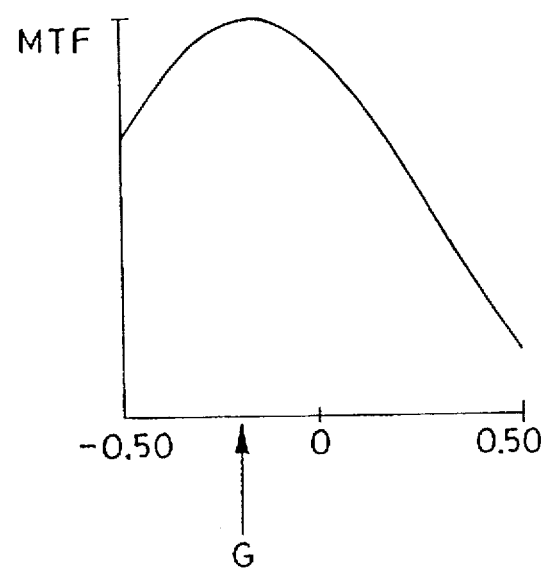
FIG. 14A and FIG. 14B show graphs illustrating MTF's of the conventional optical system for endoscopes.
Figure 14B:
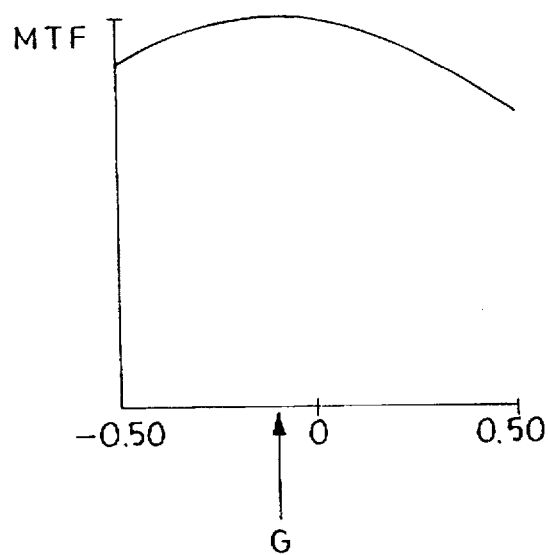

By comparing the aberration characteristics of the first embodiment of the present invention illustrated in FIG. 9A, FIG. 9B, FIG. 9C, FIG. 9D and FIG. 10 with those of the conventional example shown in FIG. 12A, FIG. 12B, FIG. 12C, FIG. 12D and FIG. 13, it will be seen that the first embodiment described above overcorrects spherical aberration. The other aberrations in the first embodiment of the present invention are maintained in conditions which are substantially the same as those in the conventional example. Further, as is seen from the MTF's of the conventional example shown in FIG. 14A and FIG. 14B, a best focus position G at an F number of 9.731 (an NA of 0.0100) of the conventional example shown in FIG. 14A is shifted 0.1 in a direction opposite to the object side from another best focus position G at an F number of 19.931 (an NA of 0.0051) shown in FIG. 14B. That is to say, the best focus position of the conventional example is shifted 0.1 in the direction opposite to the object side by narrowing an aperture of a stop disposed therein so as to change NA from 0.0100 to 0.0051. In contrast, a best focus position at the F number of 9.731 (the NA of 0.0100) of the first embodiment of the present invention shown in FIG. 11A is shifted 0.1 in a direction toward the object side to another best focus position at the F number of 19.931 (the NA of 0.0051) shown in FIG. 11B as is seen from FIG. 11A and FIG. 11B which illustrate the MTF's of the first embodiment of the present invention. That is to say, it will be understood that the best focus position of the first embodiment of the present invention is shifted 0.1 toward the object side by narrowing the aperture of the stop disposed in the first embodiment so as to change NA from 0.0100 to 0.0051.

As is understood from the foregoing description, the first embodiment of the present invention corrects the defect of the conventional example that it allows a focus point thereof to be shifted farther from the optical system by narrowing the aperture of the stop disposed therein.

For the first embodiment of the present invention described above, it is desirable to adopt, as the aspherical lens component for producing overcorrected spherical aberration (hereinafter referred to as a "lens component for shifting a depth of field toward an optical system"), a lens component which has an aspherical surface designed only with the aspherical surface coefficients E and F of the fourth and sixth orders in the formula (A) of aspherical surfaces, since such an aspherical surface is allowed to produce only spherical aberration without changing paraxial parameters of the optical system as a whole simply by defining desired values only for these coefficients. Since the "lens component for shifting a depth of field toward an optical system" is to be disposed in the vicinity of a pupil of the optical system, it is desirable also from a viewpoint of lens design with no remarkable influences on the aberrations other than spherical aberration. Further, the "lens component for shifting a depth of field toward an optical system" may be disposed in any one of the objective lens system, the relay lens system and the adaptor lens system so far as the lens component is located in the vicinity of a pupil of the optical system.

Since an optical system which produces negative spherical aberration is apt to have a depth of field shifted to a long distance from the optical system, it exhibits an effect it allows the depth of field to be shifted toward the optical system simply by correcting the negative spherical aberration. When an optical system comprises a non-flexible endoscope which is combined with an adaptor lens system as shown in FIG. 1, the optical system produces negative spherical aberration and therefore allows a best focus distance thereof to be shifted farther from it when an aperture of a stop disposed therein is narrowed. Accordingly, the optical system hardly allows a depth of field thereof to be shifted toward the optical system. However, the depth of field can be shifted toward the optical system when aspherical aberration is corrected favorably in the optical system so that an F number thereof is changed little by varying the aperture of the stop disposed therein.

For favorably correcting spherical aberration in such an optical system as that described above, it is sufficient to use an adaptor lens system which produces remarkably positive spherical aberration so as to cancel spherical aberration produced by the non-flexible endoscope. However, an adaptor lens system which is an imaging lens system is apt to produce negative spherical aberration. It is therefore difficult to compose an adaptor lens system only of spherical lens components so as to produce remarkably positive spherical aberration. For this reason, it is necessary to dispose an aspherical surface in the vicinity of a pupil of the non-flexible endoscope so that it produces positive spherical aberration with little influence on the other aberrations.

A second embodiment of the present invention is configured on the basis of the concept described above and has the numerical data listed below:

Embodiment 2
f = 1.000, F number = 9.716, image height = 0.6829

| | | |
|---|---|---|
| $r_1 = \infty$ | | |
| $d_1 = 0.1119$ | $n_1 = 1.76900$ | $v_1 = 64.15$ |
| $r_2 = \infty$ | | |
| $d_2 = 0.0320$ | | |
| $r_3 = 2.6492$ (aspherical surface) | | |
| $d_3 = 0.2079$ | $n_2 = 1.78472$ | $v_2 = 25.71$ |
| $r_4 = \infty$ | | |
| $d_4 = 0.0640$ | $n_3 = 1.58144$ | $v_3 = 40.75$ |
| $r_5 = 0.1919$ | | |
| $d_5 = 0.1279$ | | |
| $r_6 = \infty$ | | |
| $d_6 = 0.4100$ | $n_4 = 1.80610$ | $v_4 = 40.95$ |
| $r_7 = \infty$ (aperture stop) | | |
| $d_7 = 1.0869$ | $n_5 = 1.80610$ | $v_5 = 40.95$ |
| $r_8 = -0.6910$ | | |
| $d_8 = 0.0480$ | | |
| $r_9 = 1.3261$ | | |
| $d_9 = 0.4798$ | $n_6 = 1.60311$ | $v_6 = 60.70$ |
| $r_{10} = -0.5047$ | | |
| $d_{10} = 0.1599$ | $n_7 = 1.84666$ | $v_7 = 23.88$ |
| $r_{11} = -2.2140$ | | |
| $d_{11} = 0.4526$ | | |
| $r_{12} = -0.4350$ | | |
| $d_{12} = 0.1599$ | $n_8 = 1.58144$ | $v_8 = 40.75$ |
| $r_{13} = \infty$ | | |
| $d_{13} = 0.3678$ | $n_9 = 1.60311$ | $v_9 = 60.70$ |
| $r_{14} = -0.6370$ | | |
| $d_{14} = 1.1195$ | | |
| $r_{15} = 3.0272$ | | |
| $d_{15} = 6.9886$ | $n_{10} = 1.62004$ | $v_{10} = 36.25$ |
| $r_{16} = \infty$ | | |
| $d_{16} = 0.4126$ | | |
| $r_{17} = 2.2592$ | | |
| $d_{17} = -0.1599$ | $n_{11} = 1.80610$ | $v_{11} = 40.95$ |
| $r_{18} = 1.0321$ | | |
| $d_{18} = 0.4798$ | $n_{12} = 1.65160$ | $v_{12} = 58.52$ |
| $r_{19} = -4.0427$ | | |
| $d_{19} = 0.2879$ | | |
| $r_{20} = \infty$ | | |
| $d_{20} = 6.9886$ | $n_{13} = 1.62004$ | $v_{13} = 36.25$ |
| $r_{21} = -3.0272$ | | |
| $d_{21} = 1.2794$ | | |
| $r_{22} = 3.0272$ | | |
| $d_{22} = 6.9886$ | $n_{14} = 1.62004$ | $v_{14} = 36.25$ |
| $r_{23} = \infty$ | | |
| $d_{23} = 0.4126$ | | |
| $r_{24} = 2.2592$ | | |
| $d_{24} = 0.1599$ | $n_{15} = 1.80610$ | $v_{15} = 40.95$ |

-continued

| | | | |
|---|---|---|---|
| $r_{25} = 1.0321$ | | | |
| | $d_{25} = 0.4798$ | $n_{16} = 1.65160$ | $v_{16} = 58.52$ |
| $r_{26} = -4.0427$ | | | |
| | $d_{26} = 0.2879$ | | |
| $r_{27} = \infty$ | | | |
| | $d_{27} = 6.9886$ | $n_{17} = 1.62004$ | $v_{17} = 36.25$ |
| $r_{28} = -3.0272$ | | | |
| | $d_{28} = 1.2794$ | | |
| $r_{29} = 3.0272$ | | | |
| | $d_{29} = 6.9886$ | $n_{18} = 1.62004$ | $v_{18} = 36.25$ |
| $r_{30} = \infty$ | | | |
| | $d_{30} = 0.4126$ | | |
| $r_{31} = 2.2592$ | | | |
| | $d_{31} = 0.1599$ | $n_{19} = 1.80610$ | $v_{19} = 40.95$ |
| $r_{32} = 1.0321$ | | | |
| | $d_{32} = 0.4798$ | $n_{20} = 1.65160$ | $v_{20} = 58.52$ |
| $r_{33} = -4.0427$ | | | |
| | $d_{33} = 0.2879$ | | |
| $r_{34} = \infty$ | | | |
| | $d_{34} = 6.9886$ | $n_{21} = 1.62004$ | $v_{21} = 36.25$ |
| $r_{35} = -2.2592$ | | | |
| | $d_{35} = 0.5629$ | | |
| $r_{36} = \infty$ (field stop) | | | |
| | $d_{36} = 2.5620$ | | |
| $r_{37} = 3.3933$ | | | |
| | $d_{37} = 0.1439$ | $n_{22} = 1.78472$ | $v_{22} = 25.71$ |
| $r_{38} = 1.3074$ | | | |
| | $d_{38} = 0.4158$ | $n_{23} = 1.66672$ | $v_{23} = 48.32$ |
| $r_{39} = 3.0059$ | | | |
| | $d_{39} = 0.5421$ | | |
| $r_{40} = \infty$ | | | |
| | $d_{40} = 0.4798$ | $n_{24} = 1.76820$ | $v_{24} = 71.79$ |
| $r_{41} = \infty$ | | | |
| | $d_{41} = 0.5118$ | | |
| $r_{42} = \infty$ | | | |
| | $d_{42} = 1.2416$ | $n_{25} = 1.76820$ | $v_{25} = 71.79$ |
| $r_{43} = \infty$ | | | |
| | $d_{43} = 0.1599$ | $n_{26} = 1.51633$ | $v_{26} = 64.15$ |
| $r_{44} = \infty$ (aspherical surface) | | | |
| | $d_{44} = 0.4798$ | | |
| $r_{45} = \infty$ (aperture stop) | | | |
| | $d_{45} = 1.5193$ | | |
| $r_{46} = 1.5992$ | | | |
| | $d_{46} = 0.6669$ | $n_{27} = 1.81600$ | $v_{27} = 46.62$ |
| $r_{47} = 6.9506$ | | | |
| | $d_{47} = 0.4286$ | | |
| $r_{48} = -4.3899$ | | | |
| | $d_{48} = 0.4638$ | $n_{28} = 1.74077$ | $v_{28} = 27.79$ |
| $r_{49} = 1.0662$ | | | |
| | $d_{49} = 0.5341$ | | |
| $r_{50} = 2.3259$ | | | |
| | $d_{50} = 0.5469$ | $n_{29} = 1.67003$ | $v_{29} = 47.25$ |
| $r_{51} = -4.0918$ | | | |
| | $d_{51} = 0.7996$ | | |
| $r_{52} = \infty$ | | | |
| | $d_{52} = 0.1599$ | $n_{30} = 1.51633$ | $v_{30} = 64.15$ |
| $r_{53} = \infty$ | | | | aspherical surface coefficients

| | | |
|---|---|---|
| (3rd surface) | $P = 1.0000$, $E = 0.14191 \times 10$, | $F = -0.35643 \times 10$ |
| (44th surface) | $P = 1.0000$, $E = 0.10042$, | $F = -0.60555$ |

Figure 15:
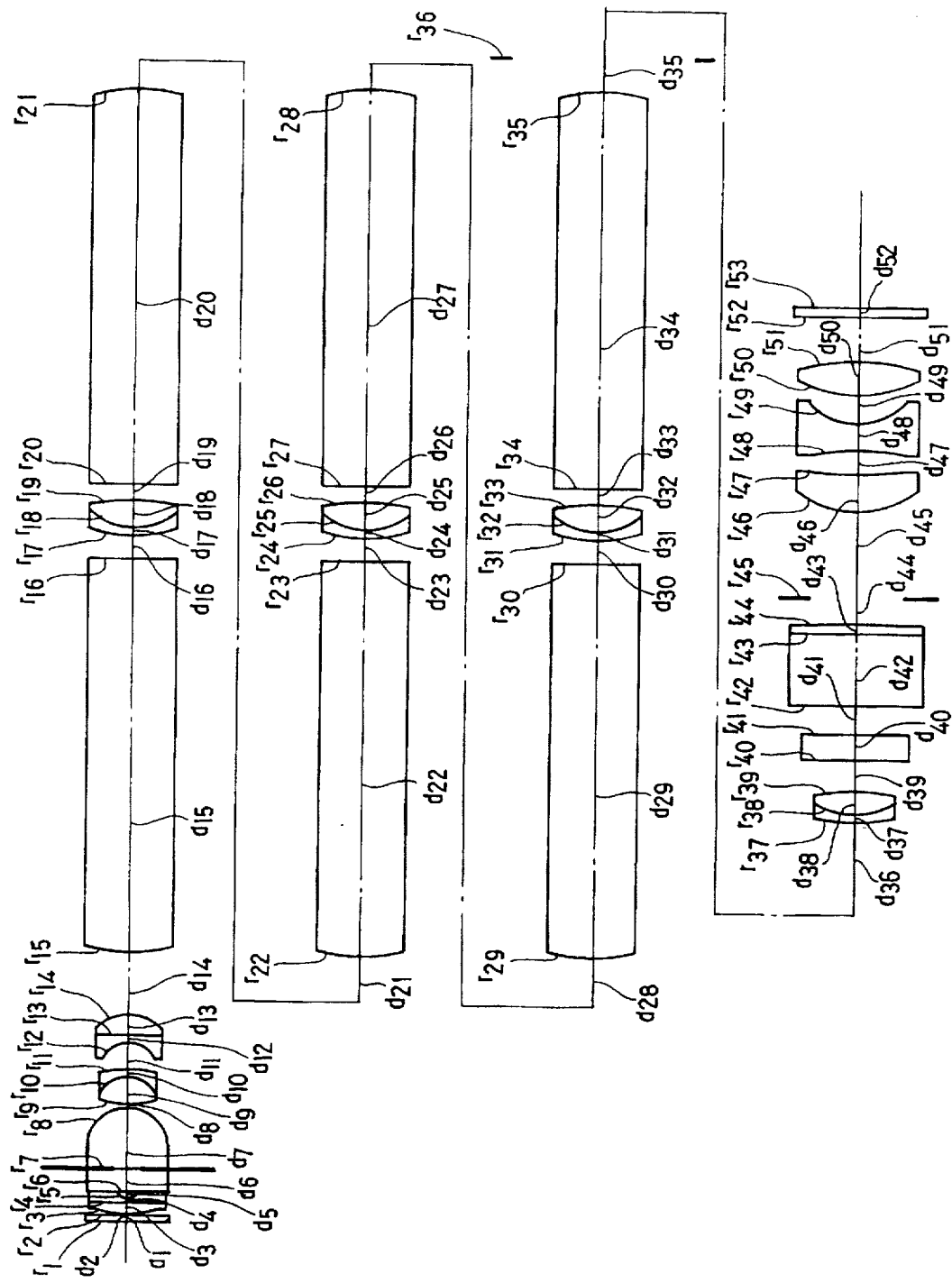
FIG. 15 shows a sectional view illustrating a composition of a second embodiment of the optical system for endoscopes according to the present invention.
Figure 16:
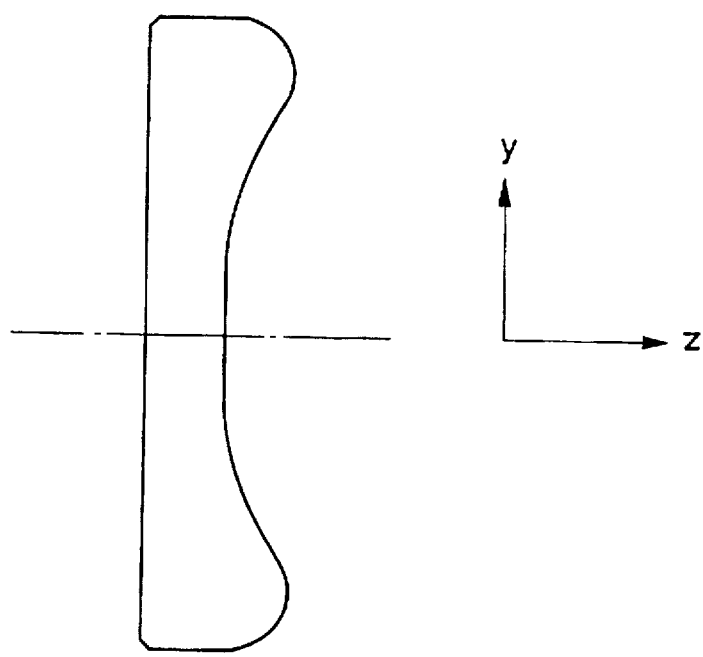
FIG. 16 shows a sectional view illustrating, on an enlarged scale, a lens component to be used in the second embodiment of the present invention.

The second embodiment of the optical system for endoscopes according to the present invention has a composition illustrated in FIG. 15 wherein a plane parallel plate ($r_{43}$ and $r_{44}$) which is transformed so as to have an aspherical surface is disposed as a "lens component for shifting a depth of field toward an optical system" in the vicinity of an aperture stop. This "lens component for shifting a depth of field toward an optical system" has a shape illustrated in FIG. 16 on an enlarged scale, or has an aspherical surface $r_{44}$. In FIG. 16, a departure from a reference sphere of the aspherical surface in the y and z directions are enlarged 200 times.

Figure 22A:
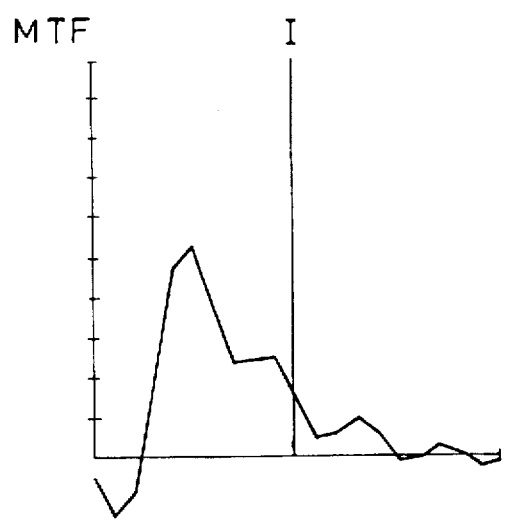
FIG. 22A through FIG. 22D show graphs illustrating MTF's of the second embodiment of the present invention in which the shifting lens component is not used.
Figure 22B:
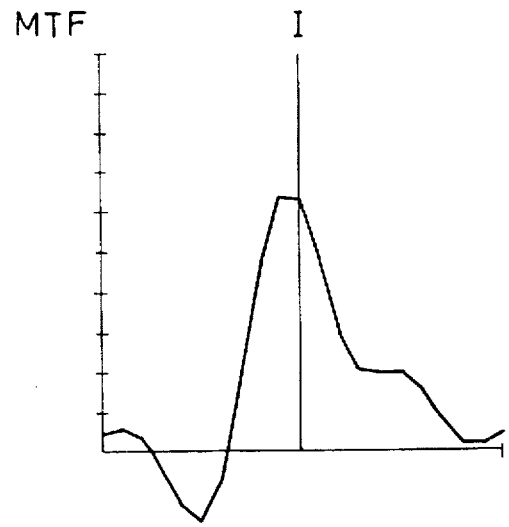
Figure 22C:
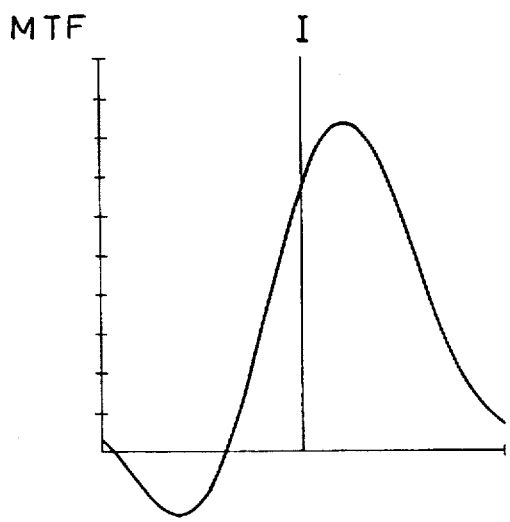
Figure 22D:
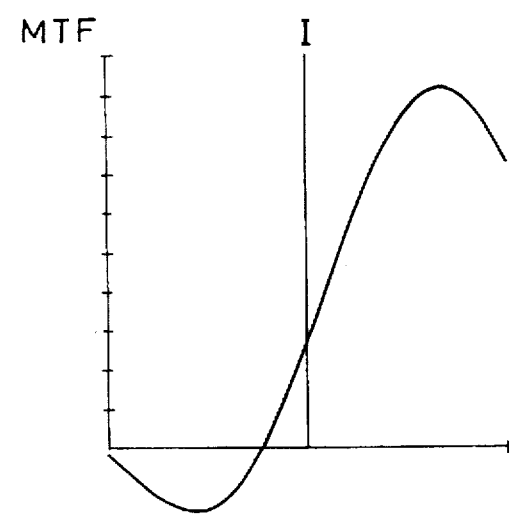

When the second embodiment does not use the "lens component for shifting a depth of field toward an optical system", it has aberration characteristics illustrated in FIG. 20A, FIG. 20B, FIG. 20C and FIG. 20D. MTF's on an optical axis in this condition of the second embodiment at different object distances are illustrated in FIG. 22A, FIG. 22B, FIG. 22C and FIG. 22D: FIG. 22A showing an MTF at an object distance of 13 mm (a long distance) and an F number of 9.7; FIG. 22B showing an MTF at an object distance of 4.8 mm (a best distance) and the F number of 9.7; FIG. 22C showing an MTF at the object distance of 4.8 mm (the best distance) and an F number of 9.7; FIG. 22C showing an MTF at the object distance of 4.8 mm (the best distance) and an F number of 18.3; and FIG. 22D showing an MTF at an object distance of 2.9 mm (a short distance) and at an F number of 18.3. These object distances are defined as distances from a leading end of the objective lens system to objects to be observed through the optical system.

Figure 21:
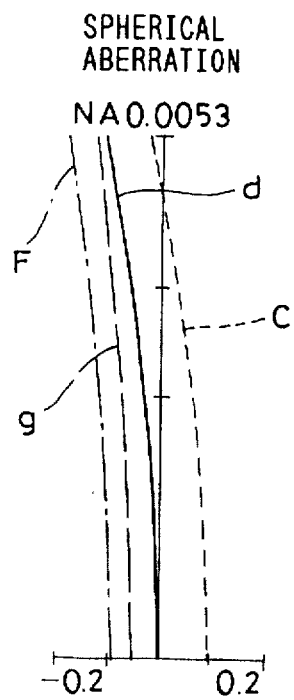
FIG. 21 shows curves illustrating spherical aberration within the narrow region of the second embodiment of the present invention in which the shifting lens component is not used.

When an aperture of a stop disposed in the second embodiment is narrowed so as to lower original brightness to a level ¼ as high (until the second embodiment has the F number of 18.3 in the condition where it does not use the "lens component for shifting a depth of field toward an optical system", it has spherical aberration illustrated in FIG. 21. Further, the MTF's of the second embodiment are varied from that illustrated in FIG. 22A to that illustrated in FIG. 22C.

Since an image is visibly blurred when an MTF becomes lower than 20%, a depth of field is defined as a range within which an MTF becomes 20% or higher by varying object distances. As is judged from FIG. 22A and FIG. 22D, a range of observation which is obtained by using the stop having the variable aperture in the second embodiment is a region delimited by borders: one which is located at 2.9 mm as measured from the best distance of 4.8 mm in a direction toward the optical system and the other located at 13 mm from the best distance of 4.8 mm in a direction away from the optical system. Though the MTF shown in FIG. 22B has a shape which is asymmetrical with regard to a predetermined design image surface I, a spot formed by a light bundle has a center of light intensity which is deviated in the negative direction due to negative spherical aberration produced by the optical system and response of the optical system is slowly lowered for objects located at longer distances due to a fact that rays within a region of small NA's are focused in the vicinity of a Gaussian image surface. This is also one of the reasons why a non-flexible endoscope has a depth of field which is large.

In contrast, the second embodiment of the present invention has aberration characteristics illustrated in FIG. 17A, FIG. 17B, FIG. 17C and FIG. 17D when it uses the above-mentioned "lens component for shifting a depth of field toward an optical system" ($r_{43}$ and $r_{44}$). When the second embodiment is set at an F number of 9.7, it exhibits spherical aberration at all NA's which is corrected favorably as shown in these drawings. When the aperture of the stop is narrowed until the optical system has an F number of 18.3, the second embodiment has spherical aberration illustrated in FIG. 18.

Figure 19A:
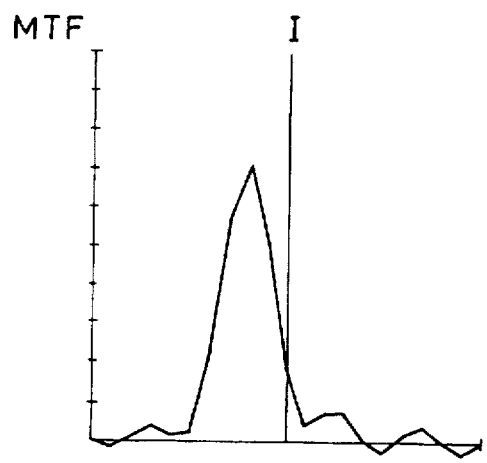
FIG. 19A through FIG. 19D show graphs illustrating MTF's of the second embodiment of the present invention.
Figure 19B:
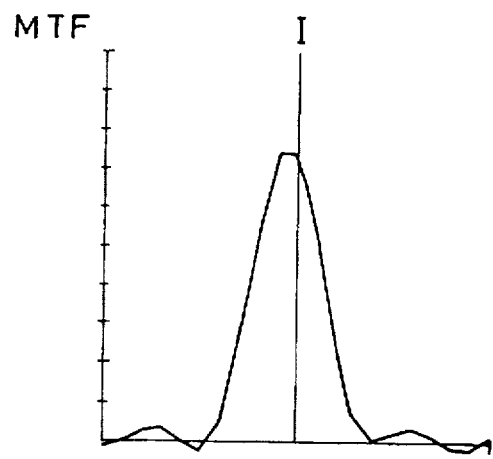
Figure 19C:
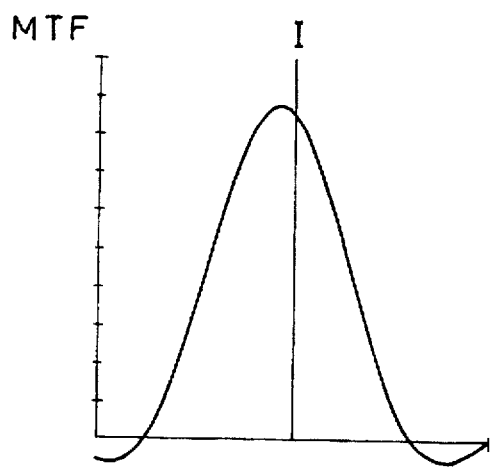
Figure 19D:
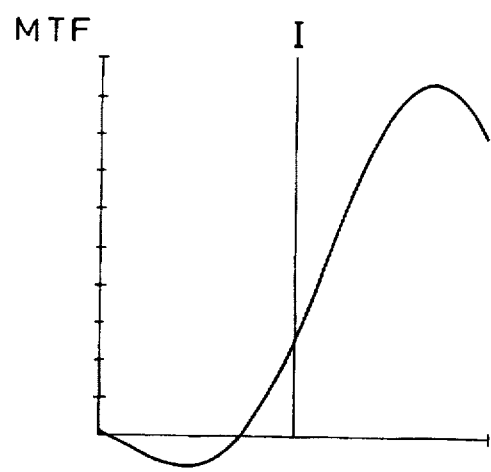

In a condition where the second embodiment uses the "lens component for shifting a depth of field toward an optical system", it has MTF's which are illustrated in FIG. 19A, FIG. 19B, FIG. 19C and FIG. 19D: FIG. 19A showing an MTF at an object distance of 6 mm (a long object distance) and an F number of 9.7; FIG. 19B showing an MTF at an object distance of 4.8 mm (a best object distance) and an F number of 9.7; FIG. 19C showing an MTF at the object distance of 4.8 mm (the best object distance) and an F number of 18.3; and FIG. 19D showing an MTF at an object distance of 2.2 mm (a short object distance) and the F number of 18.3.

As is seen from these MTF's, the MTF shown in FIG. 19B is varied to that shown in FIG. 19C by narrowing the aperture of the stop at the best object distance of 4.8 mm. These drawings clarify a fact that the second embodiment allows substantially no shift of the best image surface to be caused by varying a depth of field thereof.

Further, the second embodiment has MTF's whose shapes are made symmetrical with regard to the predetermined design image surface thereof by correcting spherical aberration as seen from these drawings.

When the second embodiment uses the "lens component for shifting a depth of field toward an optical system", it has a depth of field ranging from 2.2 mm to 6 mm as measured from the leading end of the objective lens system and is clearly improved in the depth of field on a side nearer the optical system. By comparing FIG. 17A, FIG. 17B, FIG. 17C and FIG. 17D with FIG. 20A, FIG. 20B, FIG. 20C and FIG. 20D, it will be understood that astigmatism remains substantially unchanged between the optical system using the "lens component for shifting a depth of field toward an optical system" and the optical system which does not use the lens component, and the second embodiment of the present invention which comprises the "lens component for shifting a depth of field toward an optical system" is convenient for practical use. The "lens component for shifting a depth of field toward an optical system" adopted for the optical system according to the present invention exhibits a high effect as seen from these drawings.

Figures 17A, 17B, 17C, 17D:
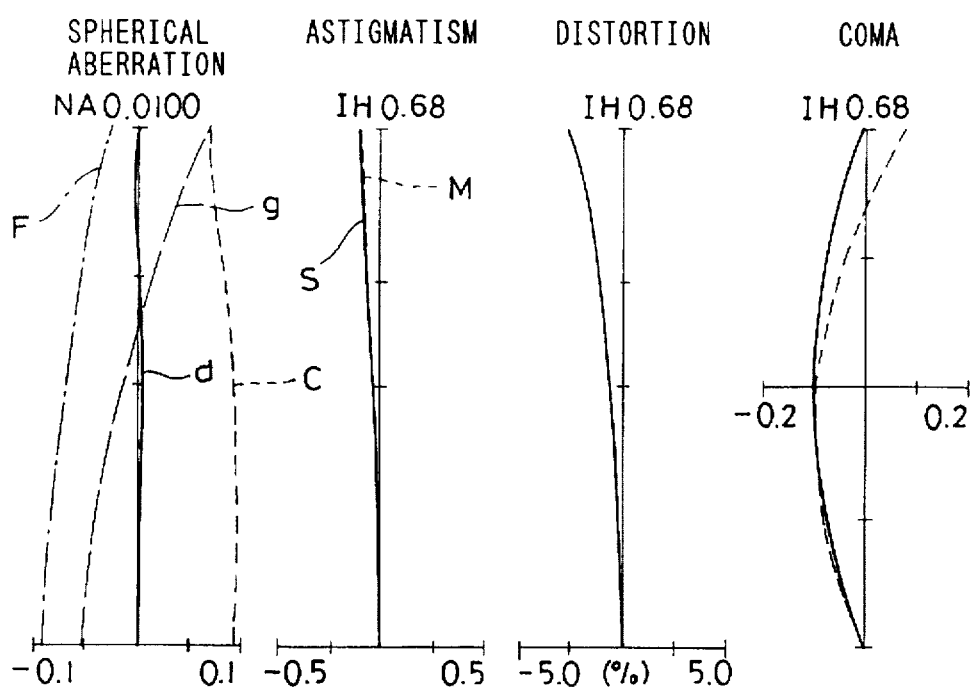
FIG. 17A through FIG. 17D show curves illustrating aberration characteristics of the second embodiment of the present invention.
Figure 18:
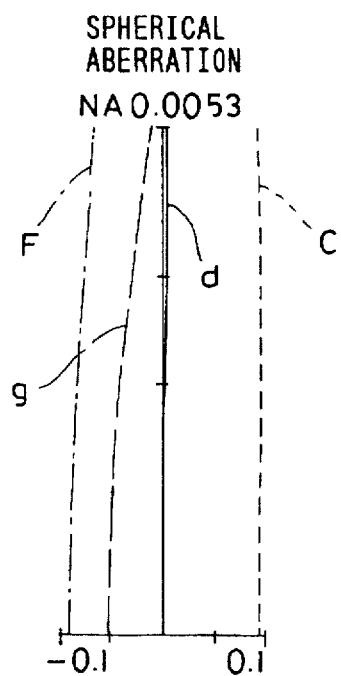
FIG. 18 shows a curve illustrating spherical aberration within a narrow NA region of the second embodiment of the present invention.
Figures 20A, 20B, 20C, 20D:
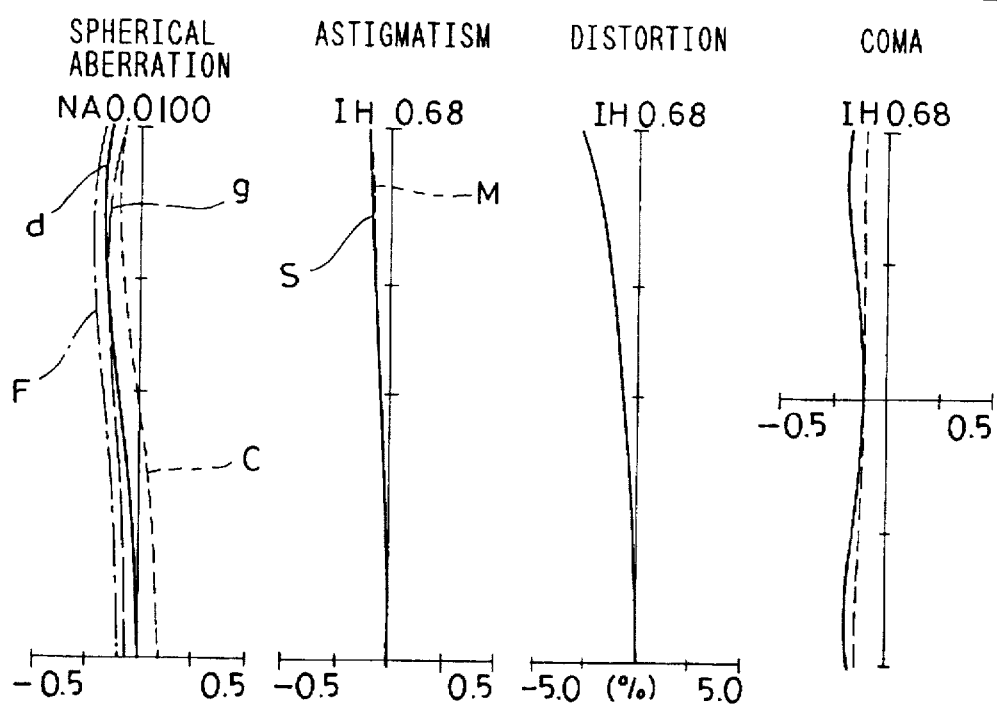
FIG. 20A through FIG. 20D show graphs illustrating aberration characteristics of the second embodiment of the present invention in which the shifting lens component is not used.

Though spherical aberration is undercorrected in the second embodiment as shown in FIG. 20A and FIG. 21 when it does not use the "lens component for shifting a depth of field toward an optical system", the spherical aberration shown in FIG. 20A and FIG. 21 can be shifted as illustrated in FIG. 17A and FIG. 18 by using the "lens component for shifting a depth of field toward an optical system". It will be understood that the aberrations other than spherical aberration remain substantially unchanged by disposing, in the vicinity of the pupil of the optical system, the "lens component for shifting a depth of field toward an optical system".

It will further be understood, from the description of the MTF's of the optical system preferred as the second embodiment, that a depth of field is improved on the side nearer the optical system by using the "lens component for shifting a depth of field toward an optical system".

That is to say, the second embodiment proves that a depth of field can be improved on the side nearer an optical system by shifting negative spherical aberration produced by an optical system toward the positive side so as to correct it nearly favorably without remarkably over-correcting spherical aberration in an optical system as a whole.

Figure 23:
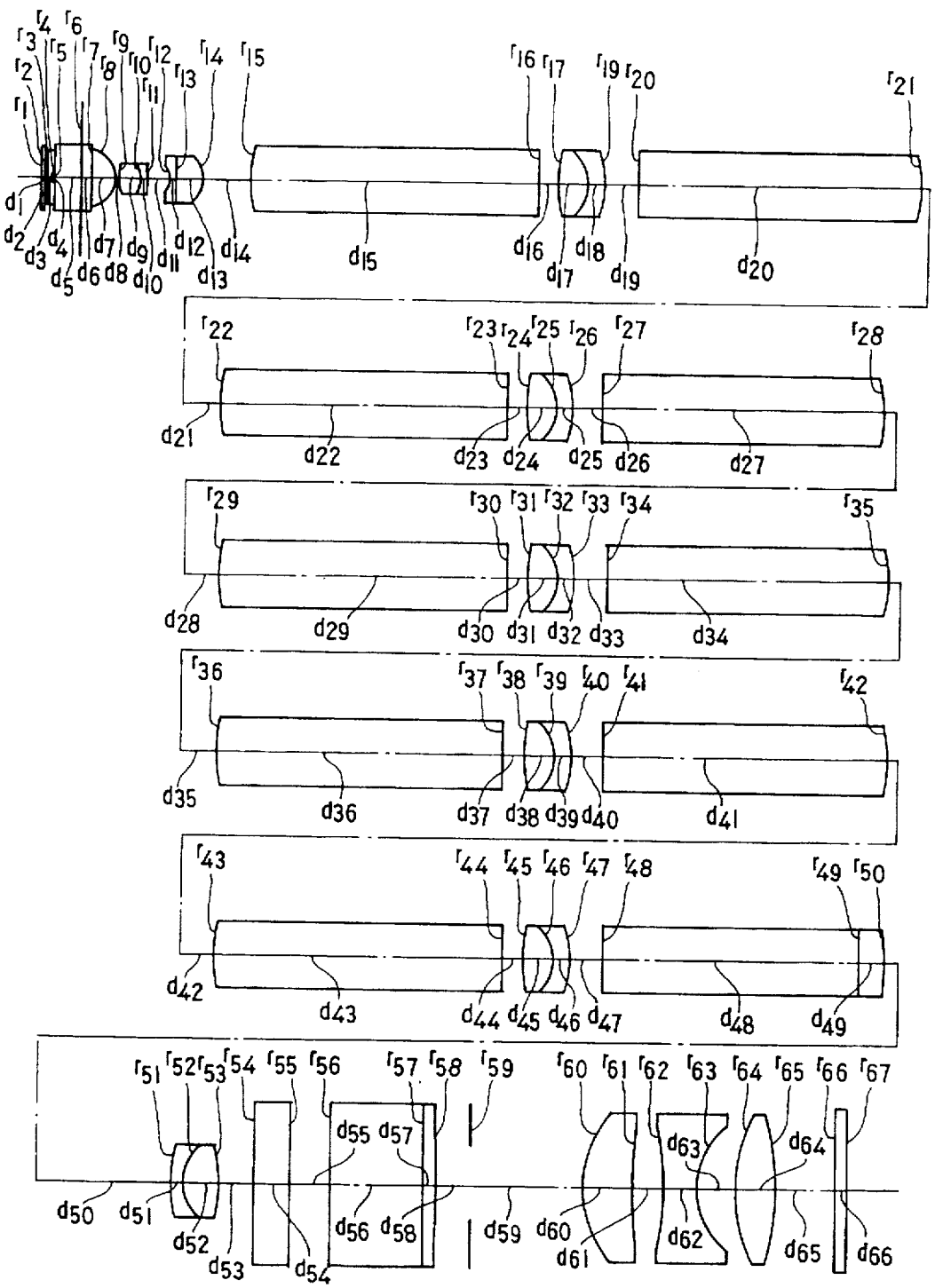
FIG. 23 shows a sectional view illustrating a composition of a third embodiment of the optical system for endoscopes according to the present invention.

Now, description will be made of a third embodiment of the optical system according to the present invention. The third embodiment has a composition illustrated in FIG. 23 and uses relay lens units having an outside diameter smaller than that of the relay lens units employed for the second embodiment, or is configured so as to be suited for use with non-flexible endoscopes having large F numbers.

Embodiment 3
f = 1.000, F number = −23.210, image height = 0.1818

$r_1 = \infty$
$d_1 = 0.0557$   $n_1 = 1.76820$   $v_1 = 71.79$
$r_2 = \infty$
$d_2 = 0.0371$
$r_3 = \infty$
$d_3 = 0.0371$   $n_2 = 1.78800$   $v_2 = 47.43$
$r_4 = 0.1262$ -continued $d_4 = 0.0557$
$r_4 = \infty$
$d_5 = 0.4253$   $n_3 = 1.88300$   $v_3 = 40.76$
$r_6 = \infty$ (aperture stop)
$d_6 = 0.1554$   $n_4 = 1.88300$   $v_4 = 40.76$
$r_7 = \infty$
$d_7 = 0.3711$   $n_5 = 1.78800$   $v_5 = 47.43$
$r_8 = -0.4419$
$d_8 = 0.0575$
$r_9 = 0.8609$
$d_9 = 0.3414$   $n_6 = 1.63854$   $v_6 = 55.38$
$r_{10} = -0.3338$
$d_{10} = 0.1113$   $n_7 = 1.84666$   $v_7 = 23.88$
$r_{11} = -1.4870$
$d_{11} = 0.3395$
$r_{12} = -0.3293$
$d_{12} = 0.0928$   $n_8 = 1.72825$   $v_8 = 28.46$
$r_{13} = \infty$
$d_{13} = 0.4082$   $n_9 = 1.77250$   $v_9 = 49.66$
$r_{14} = -0.5121$
$d_{14} = 0.7421$
$r_{15} = 2.1104$
$d_{15} = 4.4527$   $n_{10} = 1.62004$   $v_{10} = 36.25$
$r_{16} = \infty$
$d_{16} = 0.3135$
$r_{17} = 2.8764$
$d_{17} = 0.4787$   $n_{11} = 1.65160$   $v_{11} = 58.67$
$r_{18} = -0.6494$
$d_{18} = 0.2635$   $n_{12} = 1.80610$   $v_{12} = 40.95$
$r_{19} = -1.4568$
$d_{19} = 0.5213$
$r_{20} = \infty$
$d_{20} = 4.4527$   $n_{13} = 1.62004$   $v_{13} = 36.25$
$r_{21} = -2.1104$
$d_{21} = 0.7421$
$r_{22} = 2.1104$
$d_{22} = 4.4527$   $n_{14} = 1.62004$   $v_{14} = 36.25$
$r_{23} = \infty$
$d_{23} = 0.3135$
$r_{24} = 2.8764$
$d_{24} = 0.4787$   $n_{15} = 1.65160$   $v_{15} = 58.67$
$r_{25} = -0.6494$
$d_{25} = 0.2635$   $n_{16} = 1.80610$   $v_{16} = 40.95$
$r_{26} = -1.4568$
$d_{26} = 0.5213$
$r_{27} = \infty$
$d_{27} = 4.4527$   $n_{17} = 1.62004$   $v_{17} = 36.25$
$r_{28} = -2.1104$
$d_{28} = 0.7421$
$r_{29} = 2.1104$
$d_{29} = 4.4527$   $n_{18} = 1.62004$   $v_{18} = 36.25$
$r_{30} = \infty$
$d_{30} = 0.3135$
$r_{31} = 2.8764$
$d_{31} = 0.4787$   $n_{19} = 1.65160$   $v_{19} = 58.67$
$r_{32} = -0.6494$
$d_{32} = 0.2635$   $n_{20} = 1.80610$   $v_{20} = 40.95$
$r_{33} = -1.4568$
$d_{33} = 0.5213$
$r_{34} = \infty$
$d_{34} = 4.4527$   $n_{21} = 1.62004$   $v_{21} = 36.25$
$r_{35} = -2.1104$
$d_{35} = 0.7421$
$r_{36} = 2.1104$
$d_{36} = 4.4527$   $n_{22} = 1.62004$   $v_{22} = 36.25$
$r_{37} = \infty$
$d_{37} = 0.3135$
$r_{38} = 2.8764$
$d_{38} = 0.4787$   $n_{23} = 1.65160$   $v_{23} = 58.67$
$r_{39} = -0.6494$
$d_{39} = 0.2635$   $n_{24} = 1.80610$   $v_{24} = 40.95$
$r_{40} = -1.4568$
$d_{40} = 0.5213$
$r_{41} = \infty$
$d_{41} = 4.4527$   $n_{25} = 1.62004$   $v_{25} = 36.25$
$r_{42} = -2.1104$
$d_{42} = 0.7421$
$r_{43} = 2.1104$
$d_{43} = 4.4527$   $n_{26} = 1.62004$   $v_{26} = 36.25$
$r_{44} = \infty$ -continued

| | | |
|---|---|---|
| $d_{44} = 0.3135$ | | |
| $r_{45} = 2.8764$ | | |
| $d_{45} = 0.4787$ | $n_{27} = 1.65160$ | $v_{27} = 58.67$ |
| $r_{46} = -0.6494$ | | |
| $d_{46} = 0.2635$ | $n_{28} = 1.80610$ | $v_{28} = 40.95$ |
| $r_{47} = -1.4568$ | | |
| $d_{47} = 0.5213$ | | |
| $r_{48} = \infty$ | | |
| $d_{48} = 4.0223$ | $n_{29} = 1.62004$ | $v_{29} = 36.25$ |
| $r_{49} = \infty$ | | |
| $d_{49} = 0.4026$ | $n_{30} = 1.51633$ | $v_{30} = 64.15$ |
| $r_{50} = -4.6814$ | | |
| $d_{50} = 2.4686$ | | |
| $r_{51} = 2.2468$ | | |
| $d_{51} = 0.1855$ | $n_{31} = 1.78472$ | $v_{31} = 25.71$ |
| $r_{52} = 0.8377$ | | |
| $d_{52} = 0.5566$ | $n_{32} = 1.67003$ | $v_{32} = 47.25$ |
| $r_{53} = -2.3558$ | | |
| $d_{53} = 0.5325$ | | |
| $r_{54} = \infty$ | | |
| $d_{54} = 0.5566$ | $n_{33} = 1.76820$ | $v_{33} = 71.79$ |
| $r_{55} = \infty$ | | |
| $d_{55} = 0.5937$ | | |
| $r_{56} = \infty$ | | |
| $d_{56} = 1.4404$ | $n_{34} = 1.76820$ | $v_{34} = 71.79$ |
| $r_{57} = \infty$ | | |
| $d_{57} = 0.1855$ | $n_{35} = 1.51633$ | $v_{35} = 64.15$ |
| $r_{58} = \infty$ (aspherical surface) | | |
| $d_{58} = 0.5566$ | | |
| $r_{59} = \infty$ (aperture stop) | | |
| $d_{59} = 1.7625$ | | |
| $r_{60} = 1.8553$ | | |
| $d_{60} = 0.7737$ | $n_{36} = 1.81600$ | $v_{36} = 46.62$ |
| $r_{61} = 8.0635$ | | |
| $d_{61} = 0.4972$ | | |
| $r_{62} = -5.0928$ | | |
| $d_{62} = 0.5380$ | $n_{37} = 1.74077$ | $v_{37} = 27.79$ |
| $r_{63} = 1.2369$ | | |
| $d_{63} = 0.6197$ | | |
| $r_{64} = 2.6983$ | | |
| $d_{64} = 0.6345$ | $n_{38} = 1.67003$ | $v_{38} = 47.25$ |
| $r_{65} = -4.7469$ | | |
| $d_{65} = 0.9276$ | | |
| $r_{66} = \infty$ | | |
| $d_{66} = 0.1855$ | $n_{39} = 1.51633$ | $v_{39} = 64.15$ |
| $r_{67} = \infty$ | | | aspherical surface coefficients
P = 1.0000,  E = 0.38309,  F = −0.99225 × 10

Figures 24A, 24B, 24C, 24D:
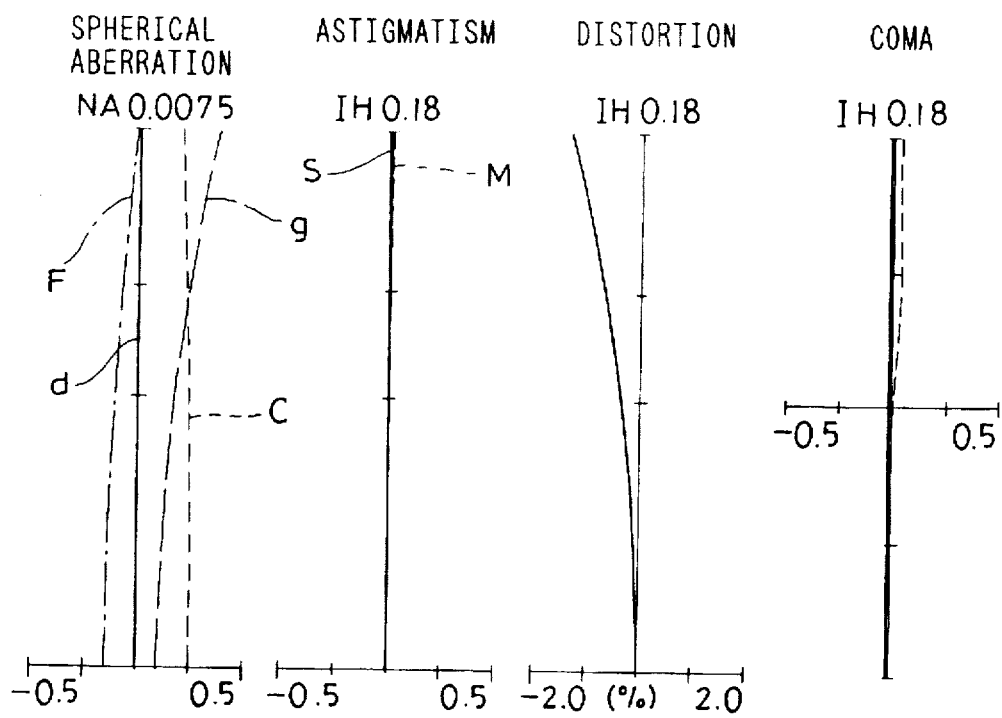
FIG. 24A through FIG. 24D show graphs illustrating aberration characteristics of the third embodiment of the present invention.
Figures 25A, 25B, 25C, 25D:
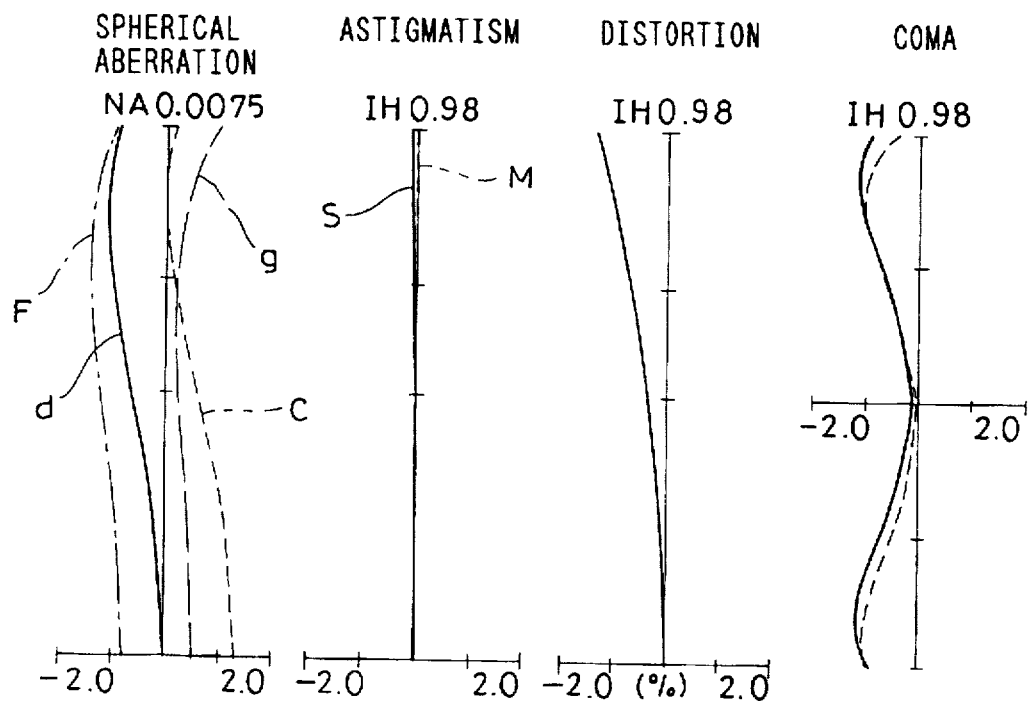
FIG. 25A through FIG. 25D show graphs illustrating aberration characteristics of the third embodiment of the present invention in which a shifting lens component is not used.

FIG. 25A, FIG. 25B, FIG. 25C and FIG. 25D illustrate aberration characteristics of the third embodiment when it does not use a "lens component for shifting a depth of field toward an optical system" and is set at an F number of 23.2, whereas FIG. 24A, FIG. 24B, FIG. 24C and FIG. 24D show aberration characteristics of the third embodiment when it uses a "lens component for shifting a depth of field toward an optical system" and is set at the F number of 23.2. The third embodiment is also configured so as to undercorrect spherical aberration as shown in FIG. 25 when it does not use the "lens component for shifting a depth of field toward an optical system" and shift spherical aberration toward the positive side as shown in FIG. 24A by using the "lens component for shifting a depth of field toward an optical system". The other aberrations remain substantially unchanged between FIG. 25 and FIG. 24A. Accordingly, the third embodiment can have a depth of field which is nearer the optical system without producing influences on the aberrations other than spherical aberration.

The third embodiment adopts a departure from a reference sphere of an aspherical surface which is larger than that selected for the second embodiment described above for correcting spherical aberration within a region where NA's are smaller. However, the "lens component for shifting a depth of field toward an optical system" adopted for the third embodiment has a fundamental shape of an aspherical surface which is similar to that shown in FIG. 26A and FIG. 26B since the third embodiment uses a non-flexible endoscope having a fundamental composition which is substantially the same as that of the non-flexible endoscope used in the second embodiment and is configured so as to produce spherical aberration having a shape which is selected on the basis of the shape of spherical aberration produced by an eyepiece lens system schematically shown in FIG. 26A.

Figure 27:
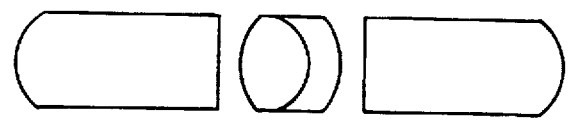
FIG. 27 shows a sectional view illustrating a composition of an ordinary relay lens unit.

A relay lens unit ordinarily has a composition wherein a cemented lens component is disposed between bar-shaped lens components as shown in FIG. 27 for relaying an image substantially with the cemented lens component only and, since surfaces of the bar-shaped lens components which are adjacent to the cemented lens component are planar, the relay lens unit shifts spherical aberration toward the negative side, thereby allowing a non-flexible endoscope to produce spherical aberration described above.

Figure 26A:
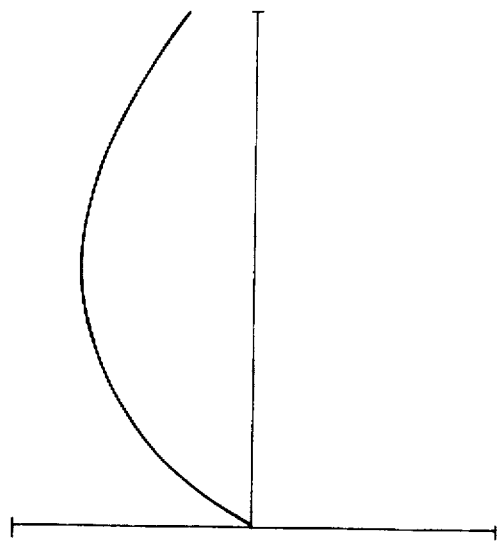
FIG. 26A and FIG. 26B show curves illustrating spherical aberration of a general eyepiece lens system and spherical aberration used for cancelling the former spherical aberration.

Even when the relay lens system has a composition different from that shown in FIG. 27, spherical aberration has a characteristics similar to that of spherical aberration illustrated in FIG. 26A. For correcting this spherical aberration, it is necessary to produce such spherical aberration as that shown in FIG. 26B. For producing such spherical aberration as that shown in FIG. 26B, it is sufficient to use a "lens component for shifting a depth of field toward an optical system" which has such a shape as that shown in FIG. 16.

Figure 26B:
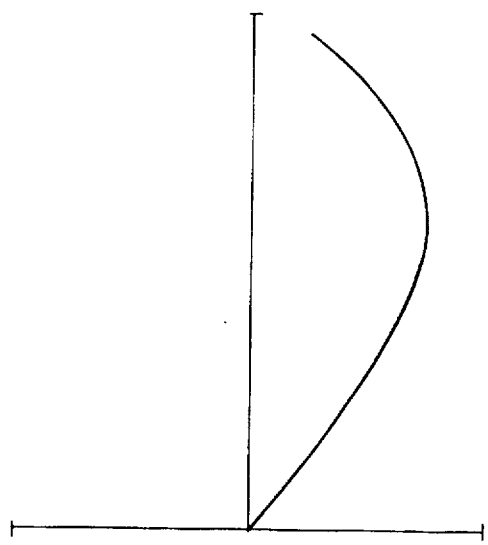

So far as spherical aberration has such a shape as that shown in FIG. 26B, a light bundle is focused in a favorable condition even while an aperture of a stop is fully open, whereby it is possible to maintain high image qualities and obtain an effect to shift a best focus position toward an optical system by narrowing the aperture of the stop by a narrowing means. For allowing an aspherical lens component to produce spherical aberration having such a shape as that shown in FIG. 26B, it is sufficient to use a lens component which has such a shape as to produce spherical aberration of low orders in the positive direction and spherical aberration of high orders in the negative direction when a spherical surface having a paraxial radius of curvature shown in FIG. 27 is taken as standard. That is to say, in case of an optical system which has an F number on the order of F numbers of optical systems for endoscopes, it is sufficient to use a lens component which has an aspherical surface having values of the aspherical surface coefficients E and F of the fourth order and the sixth order respectively within ranges defined below:

$E > 0, F < 0$

As a result, it is sufficient to use an aspherical surface of a shape which has the aspherical surface coefficients E and F satisfying the following relationship:

$E \cdot F < 0$

The "lens component for shifting a depth of field toward an optical system" which is used in each of the first through third embodiments has an aspherical surface of a shape having the aspherical surface coefficients E and F satisfying the relationship defined above. In other words, the above-mentioned condition defining the aspherical surface coefficients E and F clarifies a qualitative characteristic of the "lens component for shifting a depth of field toward an optical system" which is used in each of the first embodiment, the second embodiment and the third embodiment of the present invention.

However, spherical aberration is produced in different amounts in the first embodiment, the second embodiment and the third embodiment. Accordingly, values of the aspherical surface coefficients which are selected for the aspherical surfaces of the "lens components for shifting a depth of field toward an optical system" are different among these embodiments. That is to say, it is necessary to allow a "lens component for shifting a depth of field toward an optical system" to produce spherical aberration in an amount which is different dependently on aberrations to remain in an optical system for endoscopes to be combined with the lens component and it is difficult to specify in general an amount of spherical aberration to be produced by a "lens component for shifting a depth of field toward an optical system".

However, it is desirable to define the "lens component for shifting a depth of field toward an optical system" used in each of the embodiments of the present invention as described below:

A height $H_A$ which is the largest of those of rays incident on the "lens component for shifting a depth of field toward an optical system" used in the second embodiment has a value of $h_2=0.284$ at an F number of 9.7 when a focal length of the optical system as a whole is taken as 1. In this condition, $E_2 \cdot h_2^4 = 6.533 \times 10^{-4}$ and $F_2 \cdot h_2^6 = 3.177 \times 10^{-4}$.

In the optical system preferred as the third embodiment, a height h which is the largest of those of rays incident on the "lens component for shifting a depth of field toward an optical system" has a value of $h_3=0.137$ at an F number of 23.2. In this condition, $E_3 \cdot h_3^4 = 1.35 \times 10^{-4}$ and $F_3 \cdot h_3^6 = 6.56 \times 10^{-5}$. These values are nearly constant owing to a fact that aberrations remaining in the optical systems used in the non-flexible endoscopes have shapes which remain substantially unchanged between the second embodiment and the third embodiment.

Image qualities are degraded by using, at the NA selected for the second embodiment, the "lens component for shifting a depth of field toward an optical system" which is adopted for the third embodiment. In this case, $E_3 \cdot h_2^4 = 2.5 \times 10^{-3}$, $F_3 \cdot h_2^6 = 5.21 \times 10^{-3}$, and an NA and a departure from a reference sphere which make the optical system unusable can be defined experimentally. Speaking concretely, it is possible to obtain an effect to "shift a depth of field toward an optical system" without degrading image qualities when the following relationship is satisfied:

$$Mh^m < 5.21 \times 10^{-3}$$

wherein the reference symbol M represents an aspherical surface coefficient of the m'th order of an aspherical surface of a "lens component for shifting a depth of field toward an optical system" which produces spherical aberration in an excessive amount and the reference symbol h designates a height of a ray incident on the "lens component for shifting a depth of field toward an optical system".

Figure 28A:
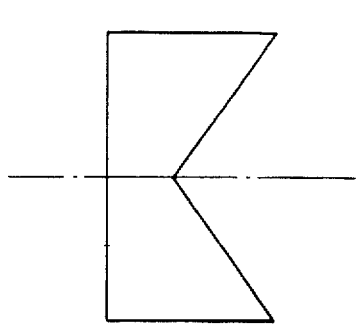
FIG. 28A and FIG. 28B show diagrams illustrating another example of a "lens component for shifting a depth of field toward an optical system" to be used in the optical system for endoscopes according to the present invention.
Figure 28B:
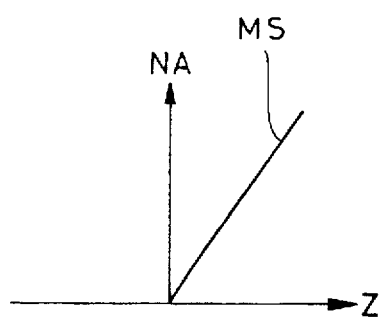

Further, a prism lens component such as that shown in FIG. 28A is usable as a "lens component for shifting a depth of field toward an optical system". This lens component also produces positive spherical aberration such as that shown in FIG. 28B and can exhibit an effect which is similar to that obtained by each of the aspherical lens components used in the embodiments of the present invention described above.

A lens component which produces spherical aberration such as the "lens component for shifting a depth of field toward an optical system" described above is used mainly for producing spherical aberration in a predetermined amount and may have any paraxial refractive power. It is rather desirable that such a lens component is a lens component (or an optical element) which has nearly no paraxial refractive power. Speaking concretely, a lens component (or an optical element) which has nearly no refractive power can be disposed in an optical system for varying only spherical aberration in the optical system and is therefore applicable to various types of lens systems.

It is required for endoscopes these days to have resistance to autoclaving. Autoclaving (autoclave sterilization) is a method for sterilizing all germs by keeping them standing in a high-pressure steam at a temperature of 135°, for example, for five minutes. Autoclaving is a sterilizing method which is relatively low cost among sterilization methods for medical instruments. Although there are non-flexible endoscopes which are resistant to autoclaving on the market, there have been no external TV cameras for endoscopes which have are resistant to autoclaving. Under the present circumstances where external TV cameras for endoscopes are frequently used for surgical operations while monitoring through endoscopes, it is desired to develop external TV cameras which are resistant to autoclaving.

In order that a TV camera is resistant to autoclaving, however, the TV camera must withstand hundreds of surgical operations under conditions of high-pressure high temperature steam, as described above, or other extreme environments. For obtaining a TV camera which is resistant to resistant to autoclaving, it is necessary to make a TV camera head completely airtight. However, it is impossible to make an external TV camera for endoscopes completely airtight since it comprises movable parts for adjusting a focused condition of an optical system for endoscopes. When a focusing knob is packed with an O-ring, for example, the focusing knob requires too strong a force for turning by human power and the O-ring becomes ineffective due to deterioration of the rubber before it is used for hundreds of surgical operations. It is therefore necessary, for obtaining a TV camera which is resistance to autoclaving, to configure a pan-focus TV camera head which has no focusing mechanism. Such a camera head can be configured by using an aspherical lens component such as those used in the first through third embodiments of the present invention described above.

Further, since a TV camera which is resistant to autoclaving has a complicated structure and has a high manufacturing cost, it is required to obtain a TV camera head which can be manufactured at a cost as low as that for the conventional TV camera head which is not resistant to autoclaving.

It is therefore desirable to prepare and use selectively two types of TV camera heads for an external TV camera for endoscopes: one which is nearly of the pan-focus type, has no focusing function and permits autoclaving; and the other of the conventional type which has a focusing function and does not permit autoclaving.

A camera head such as either of the two types described above does not comprise a stop having variable aperture and does not require the no use of an aspherical lens component such as that used in each of the first through third embodiments of the present invention.

When the aspherical lens component which is used for producing spherical aberration in the optical system according to the present invention is configured so as to have substantially no refractive power as already described above, the paraxial refractive power distribution is not substantially changed by disposing or removing the aspherical lens component into or out of an optical path in the optical system. Accordingly, optical systems for the two types of camera heads described above can have a common composition, except for the aspherical lens component which is to be used only one of the optical systems, and are remarkably advantageous from a viewpoint of manufacturing cost.

In addition, great convenience can be obtained by configuring a camera head so as to have a structure which permits disposing and removing the aspherical lens component into and out of an optical path of an optical system disposed therein so that a single type of camera head can have the functions of the two types of camera heads described above.

An aspherical surface which is to be used in a field of cameras, for example, has an optical power, contributes to establish paraxial imaging relationship and has a role to favorably correct aberrations in a lens system by producing aberrations. In contrast, the aspherical lens component which is used for producing spherical aberration in the optical system according to the present invention is to be configured desirably as a lens component having no refractive power, and is different definitively from lens components which are to be used in cameras. It is desirable that the aspherical lens component having nearly no refractive power (a "lens component for shifting a depth of field toward an optical system") is obtained by forming an aspherical surface on an optical element which is similar to a plane parallel plate. At a practical stage to obtain a shaped lens component, a contact type surfacial shape measuring instrument is used for measuring a shape of the shaped lens component. This measuring instrument requires an input of a paraxial radius of curvature in three or a small number of digits and provides an output which can be regarded as indicating a parallel condition.

Though the lens component for producing spherical aberration described above (optical axis element) is disposed in a TV camera in each of the embodiments described above, the lens component may be disposed in a relay lens system. When a "lens component for shifting a depth of field toward an optical system" is disposed in the relay lens system used in the second embodiment, for example, the "lens components for shifting a depth of field toward an optical system" are used in both the relay lens system and the TV camera. Since the optical system preferred as the second embodiment is configured so as to correct spherical aberration favorably in the optical system as a whole by the "lens component for shifting a depth of field toward an optical system" which is disposed in the TV camera (in which spherical aberration is almost zeroed as shown in FIG. 17A), spherical aberration produced by the optical system as a whole can be shifted toward the positive side (to the vicinity of an image surface thereof), as in the optical system preferred as the first embodiment, by disposing, also in the relay lens system, the "lens component for shifting a depth of field toward an optical system".

So far as an optical system comprises a relay lens system and has spherical aberration which is corrected almost to zero as described above, like the optical system preferred as the second embodiment of the present invention, it is possible to obtain positive spherical aberration in the optical system as a whole by disposing an additional "lens component for shifting a depth of field toward an optical system" in the relay lens system or correct spherical aberration almost to zero even when the relay lens system is exchanged with another relay lens system which does not comprise the "lens component for shifting a depth of field toward an optical system" and produces negative spherical aberration. It is therefore possible, even in the latter case, to obtain the effect "to shift a depth of field toward an optical system".

An optical system in which spherical aberration is nearly zeroed by using an aspherical surface in a TV camera, like the optical system preferred as the second embodiment of the present invention, is not only an optical system having favorably corrected spherical aberration but also can have different kinds of effects "to shift a depth of field toward an optical system" by configuring the optical system as an external TV camera for endoscopes which comprises the imaging lens system etc. used in the TV camera for the optical system and attaching the external TV camera for endoscopes to a non-flexible endoscope which comprises an objective lens system and a relay lens system.

Figure 29A:
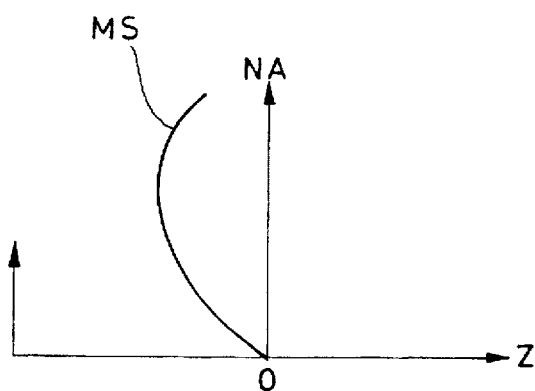
FIG. 29A and FIG. 29B show diagrams illustrating spherical aberration and an MTF thereof.
Figure 29B:
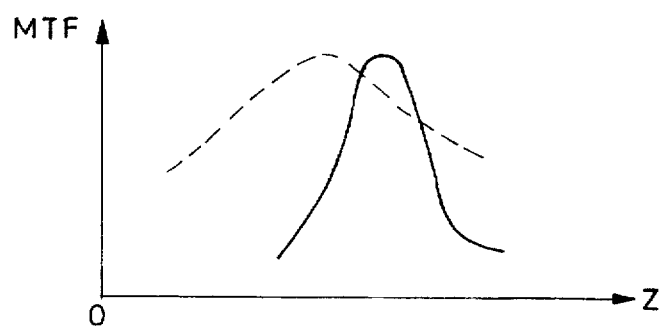

The object of the present invention can be accomplished also by disposing an aperture control mechanism at a location of a pupil of an optical system which has negative spherical aberration as shown in FIG. 29A, fully opening an aperture of a stop for locating a depth of field far from the optical system and narrowing the aperture of the stop for locating the depth of field near the optical system. In this case, an MTF which is obtained by fully opening the aperture of the stop which is traced in the solid line in FIG. 29B is varied into another MTF traced in the dashed line which is obtained by narrowing the aperture of the stop. A best image surface is shifted toward the object side and a depth of field is improved by narrowing the aperture of the stop as seen from FIG. 29B.

Figure 30A:
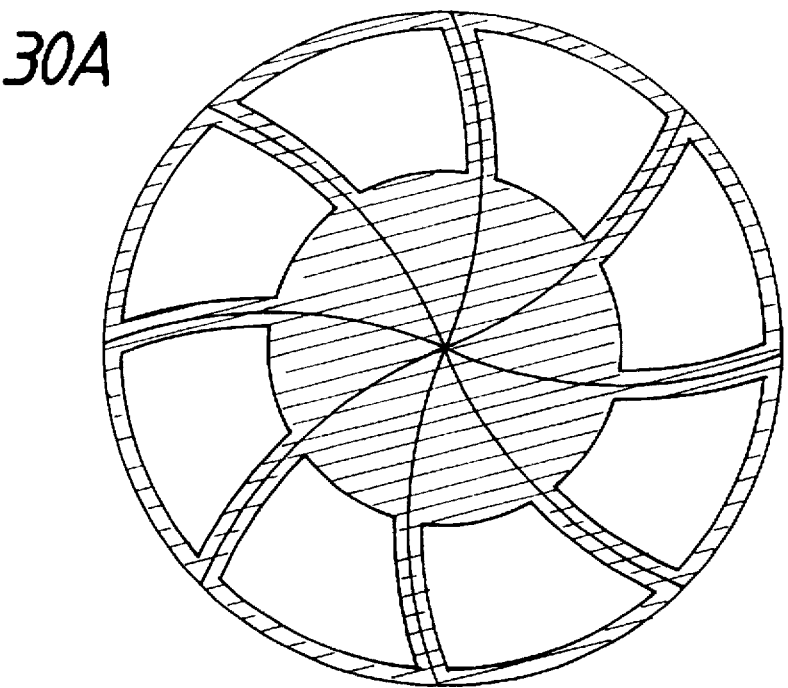
FIG. 30A and FIG. 30B show plan views illustrating a shape of a stop for shifting a focus point to a best location thereof which is to be used in the optical system using the "lens component for shifting a depth of field toward an optical system"
Figure 30B:
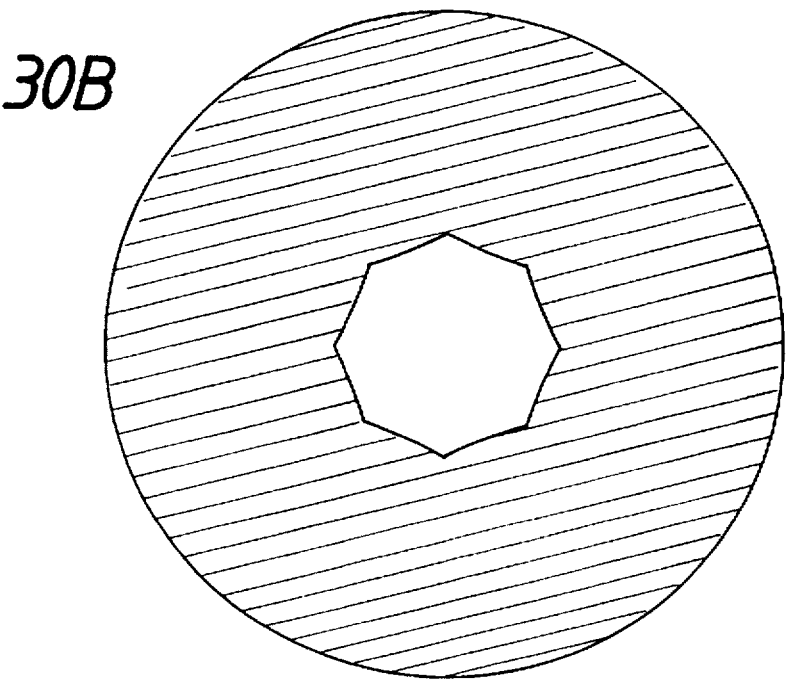

For obtaining the function described above, it is conceivable to use either of the stops illustrated in FIG. 30A and FIG. 30B.

Figure 31A:
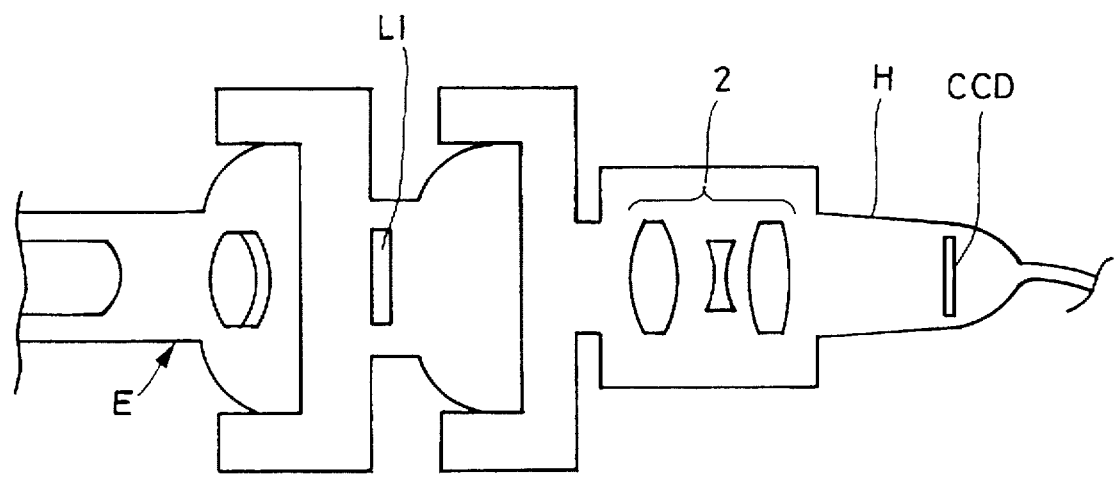
FIG. 31A and FIG. 31B show sectional views exemplifying disposition of the "lens component for shifting a depth of field toward an optical system" in an endoscope.
Figure 31B:
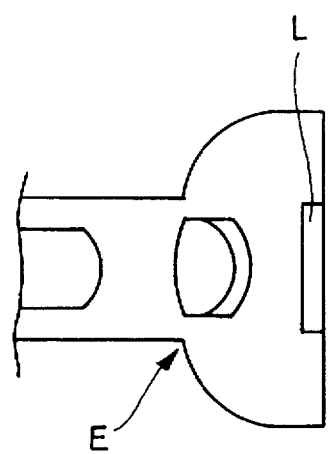

FIG. 31A and FIG. 31B exemplify locations at which the above-mentioned "lens component for shifting a depth of field toward an optical system" is to be disposed: FIG. 31A showing an example wherein a "lens component for shifting a depth of field toward an optical system" L is disposed between an eyepiece lens unit E and a TV camera head H; whereas FIG. 31B showing another example wherein a "lens component for shifting a depth of field toward an optical system" L is disposed so as to be serve also as a cover glass plate for an eyepiece lens unit E of a non-flexible endoscope.

Figure 32A:
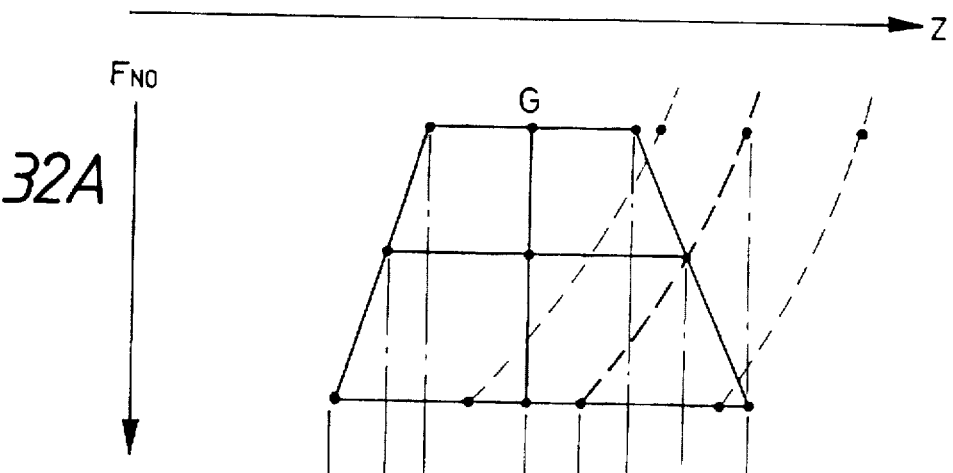
FIG. 32A, FIG. 32B and FIG. 32C show diagrams illustrating relationships between F numbers and depths of field.
Figure 32B:
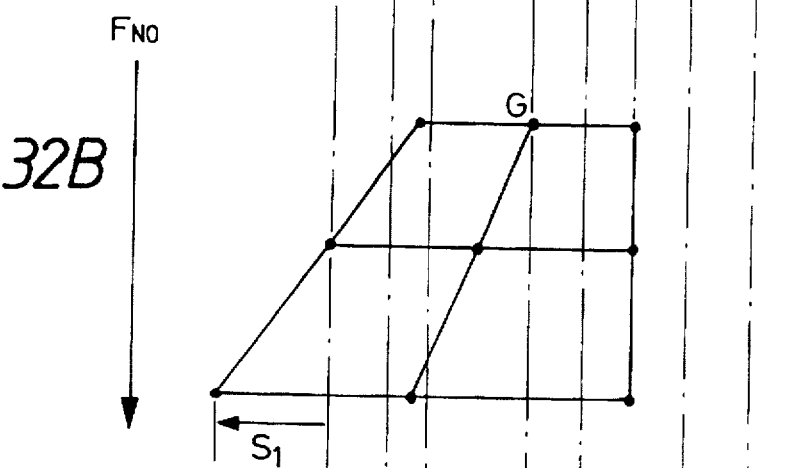
Figure 32C:
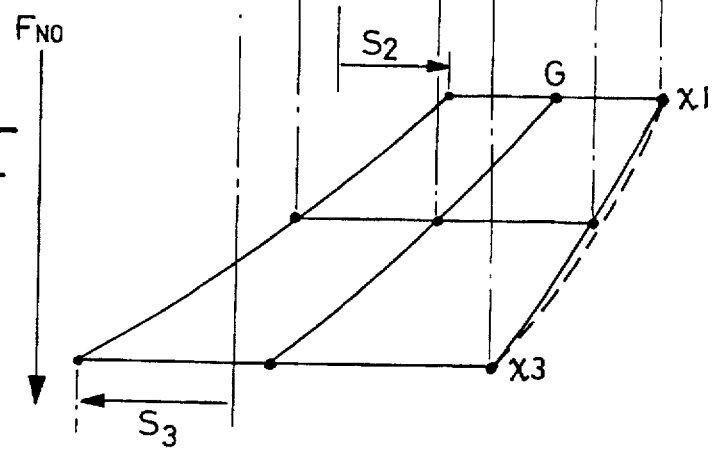

Now, description will be made of an amount of spherical aberration which is to be produced by an ideal "lens component for shifting a depth of field toward an optical system". FIG. 32A, FIG. 32B and FIG. 32C illustrate relationship between F numbers and depths of field (Z). In these drawings, depths of field (z) are farther from an optical system in the direction indicated by the arrow. An ordinary optical system has a best image surface G at a location which is constant independently of F numbers thereof and a depth of field which is larger as the F numbers thereof is enlarged (in a direction indicated by an arrow). Further, a "lens component for shifting a depth of field toward an optical system" shifts a best image surface toward an optical system as F numbers are larger. Accordingly, this lens component shifts a depth of field as a whole nearer an optical system as indicated by the arrow S. When it is assumed that the depth of field is widened toward the optical system with a side thereof farther from the optical system remaining unchanged as shown in FIG. 32B, spherical aberration to be obtained in this case can be defined as described below:

When the lens component is configured so as to overcorrect spherical aberration as shown in FIG. 33A, FIG. 33B, FIG. 33C and FIG. 33D, a distance as measured from a best image surface in a condition where an aperture of a stop is fully open to another best image surface in a condition where the aperture of the stop is narrowed is represented by $\Delta z$, NA's in both the conditions are designated by $NA_1$ and $NA_2$ respectively ($NA_1 < NA_2$), and diameters of circles of confusion are denoted by $\phi_1$ and $\phi_2$ respectively ($\phi_1 < \phi_2$), $\phi_1$ and $\phi_2$ are expressed as follows:

$$\phi_1 = 2NA_1(\Delta z + x)$$

$\phi_2 = 2NA_2 x$

A value of x giving $\phi_1 = \phi_2$ is:

$x = NA_1 \Delta z/(NA_1 + NA_2)$

For preventing $\phi_1$ and $\phi_2$ from exceeding a range of blurring allowed for image pickup devices, it is necessary to obtain the following relationship:

$\phi \leq 2KP$ wherein the reference symbol $\phi$ represents a diameter of an allowable circle of confusion, the reference symbol P designates a pitch of the image pickup devices and the reference symbol K denotes a coefficient which is determined taking into consideration variations of response of an imaging optical system as a whole to be caused due to transmission through optical low pass filters, electrical enhancement and so on, or is ordinarily regarded as nearly equal to 5.

By arranging the formulae mentioned above, $\Delta z$ can be defined as follows:

$\Delta z \leq 5P\{(1/NA_2)-(1/NA_1)\}$

Figure 34A:
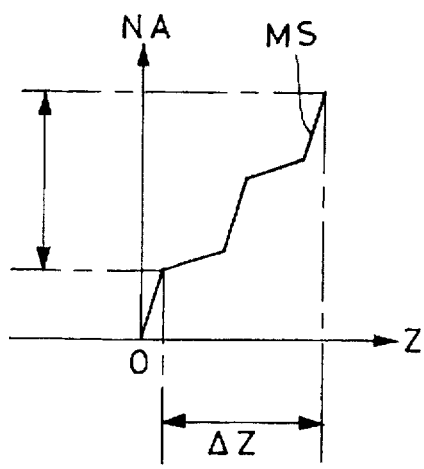
FIG. 34A and FIG. 34B show graphs illustrating other examples of overcorrected spherical aberration.
Figure 34B:
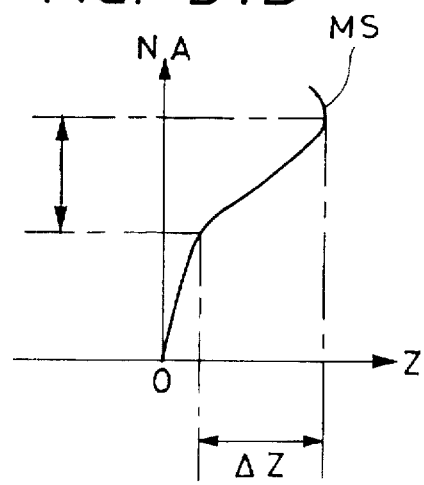
Figure 35:
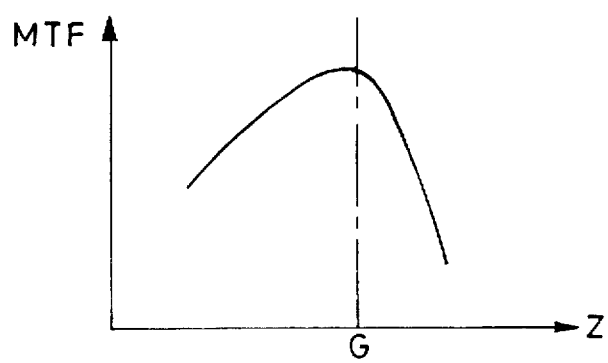
FIG. 35 shows a graph illustrating an MTF of an optical system having overcorrected spherical aberration.
Figure 36:
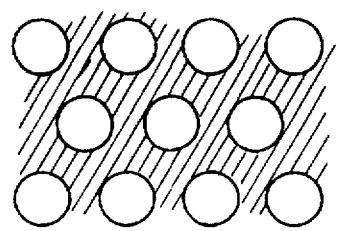
FIG. 36 shows a diagram illustrating an outline of an image of an end surface of an optical fiber bundle.

That is to say, it is sufficient for preventing $\phi_1$ and $\phi_2$ from exceeding the allowable range of blurring to limit, within the range defined above, the distance $\Delta z$ as measured from the best image surface in the condition where the aperture of the stop is fully open to the best image surface in the condition where the aperture of the stop is narrowed. Further, positive spherical aberration may have any shape (a curve of spherical aberration may have any shape) so far as $\Delta z$ is within the range defined above. For example, positive spherical aberration may have a shape shown in FIG. 34A or FIG. 34B.

In case of the conventional endoscope apparatus which irradiates an object with rays emitted from a light source and uses reflected rays for observation, a limit of brightness permitting observation is determined dependently on luminance of the light source, a distance to the object and an F number of an observation optical system disposed in the endoscope apparatus in particular when the object is located at a long distance. Therefore, the limit of brightness (a depth of brightness) is as indicated by the dashed lines in FIG. 32A.

The endoscope apparatus according to the present invention has an improved depth of field, but may not exhibit sufficiently the effect provided by the present invention when illuminating rays do not reach sufficiently to an object. For this reason, it is more desirable to coincide a side of a depth of field which is farther from an optical system with a curve of depth of brightness as shown in FIG. 32C, thereby effectively improving a depth of field. In this case, it is possible to obtain a remarkably large depth of field by setting a best distance on the side farther from an optical system (indicated by the arrow $S_2$) which is far brighter than that shown in FIG. 32A before narrowing the aperture of the stop and setting a best distance on the side nearer the optical system (indicated by the arrow $S_3$) after the aperture of the stop is narrowed.

Though the optical system according to the present invention is configured so as to shift a best image surface toward an optical system by varying a diameter of an aperture (by narrowing an aperture of a stop) in the foregoing description, it is possible to obtain an effect to improve a depth of field to a certain degree simply by overcorrecting spherical aberration produced by an optical system.

Figure 33A:
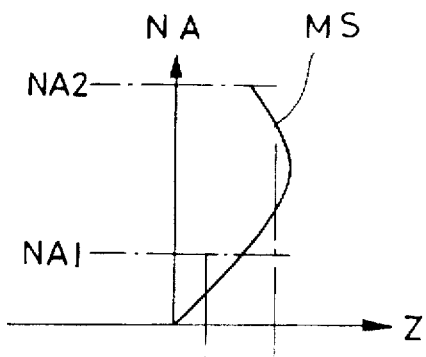
FIG. 33A through FIG. 33D show diagrams illustrating relationships among apertures, shift distances of locations of best image surface and diameters of circles of confusion of an optical system having overcorrected spherical aberration.
Figure 33B:
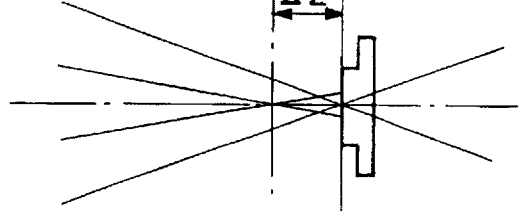
Figure 33C:
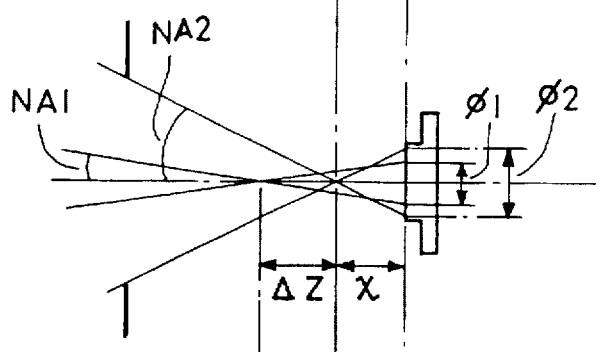
Figure 33D:
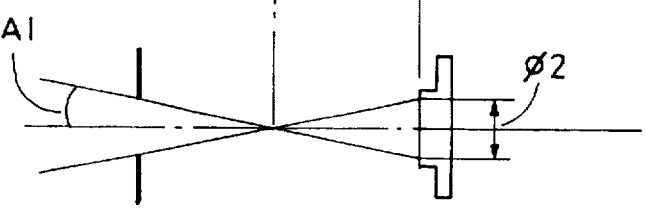

When an optical system produces spherical aberration as shown in FIG. 33A, for example, rays are focused on the image side of a best image surface and the optical system exhibits response to objects located on the object side of the best image surface, thereby making it possible to obtain the effect described above. This tendency is remarkable at high frequencies in particular, and an optical system having such a characteristic has response which is higher for objects located at shorter distances or exhibits a depth of field improved for the objects located at the shorter distances.

An optical system for non-flexible endoscopes which produces negative spherical aberration, in contrast, exhibits a nature to have a depth of field improved for objects located at long distances and correction of this spherical aberration results in improvement of the depth of field which is insufficient for objects located at short distances. Accordingly, the "lens component for shifting a depth of field toward an optical system" used in the optical system according to the present invention has a role to improve a depth of field or is effective for improving a depth of field which is insufficient.

In addition to the endoscope apparatus equipped with non-flexible endoscopes using relay lens systems, there are available endoscope apparatus which are equipped with fiber scopes using optical fibers. The endoscope apparatus which are equipped with the fiber scopes may allow moiré stripes to be produced due to interference between images formed on end surfaces of optical fiber bundles and sampling points of CCD's.

The optical system which has a depth of field enlarged on the side nearer the optical system described above produces spherical aberration in rather a large amount and can exhibit also an effect to eliminate moiré when it is set so as to blurr highly intense frequency spectra produced by the end surfaces of the optical fiber bundles and attaching a fiber scope to the optical system with an aperture of a stop disposed therein fully open.

The endoscope apparatus according to the present invention is configured so as to produce overcorrected spherical aberration so that it is capable of improving a depth of field thereof for objects located at short distances by narrowing an aperture of a stop which is set for objects located at long distances so as to shift a best image surface toward the object side and is free from tedious focusing operation.

We claim:

1. An optical system comprising: a stop means having a variable aperture and a lens system; wherein said optical system produces aberrations which are controlled so as to prevent an image surface thereof from shifting from the object side to the image side by narrowing the aperture of said stop means.

2. An optical system according to claim 1 wherein a best focus position is shifted, owing to said aberrations, so as to be set for an object located at long distances when the aperture is fully open and for objects located at short distances when the aperture is narrowed in conjunction with opening and closing of said stop means.

3. An optical system according to claim 1 wherein a best focus position remains unchanged regardless of opening and closing of said stop means.

4. An optical system according to claim 1 wherein said optical system produces spherical aberration, wherein a best focus position of said optical system is shifted by opening and closing said stop means, and wherein said spherical aberration is controlled so as to maintain a side of a depth of field thereof which is located farther therefrom substantially at a constant location at different diameters of the aperture of said stop means.

5. An optical system according to claim 1 wherein said optical system produces spherical aberration, wherein a best focus position of said optical system is shifted, owing to the spherical aberration, by opening and closing said stop means and wherein said spherical aberration is controlled so as to maintain constant brightness on an image of an object at different diameters of the aperture of said stop means.

6. An endoscope according to any one of claims 1, 2, 3, 4 and 5 further comprising: an optical system and an illuminating means for irradiating an object with illuminating rays.

7. An optical system according to claim 6 wherein the aperture of said stop means is varied dependently on a variation of illuminance on an image surface caused in conjunction with a variation of a distance as measured from said optical system to an object to be observed.

8. An optical system according to claim 6 wherein said optical system comprises an aspherical surface which has a shape expressed by the formula shown below and satisfies the following condition:

$$E \cdot F < 0$$

$$Sag = (h^2/r)\sqrt{1 + (1 - p(h/r)^2)} + Eh^4 + Fh^6 + \ldots$$

wherein the reference symbol h represents a height of a ray passing through the aspherical surface, the reference symbol Sag designates a value, in a direction along an optical axis on a coordinates system, of a point at a height of h on the aspherical surface (on an assumption that Sag has a value of 0 when h is equal to 0), the reference symbol r designates a radius of curvature on a portion of the aspherical surface located on the optical axis (a radius of curvature on a reference sphere of the aspherical surface), and the reference symbols p, E, F, . . . denote aspherical surface coefficients.

9. An endoscope apparatus comprising: an illuminating means for irradiating an object and an optical system for forming an image of an object onto solid-state image pickup devices; wherein a stop means having a variable aperture is disposed in said optical system, wherein said optical system produces aberrations and wherein said aberrations are controlled so as to prevent a best image surface due to said aberrations from being shifted from the image side to the object side by narrowing the aperture of said stop means.

10. An endoscope apparatus according to claim 7 wherein said aberrations are controlled so as to shift a location at which rays are focused in a best condition from the object side to the image side by narrowing the aperture of said stop means.

11. An endoscope apparatus according to claim 9 wherein said aberrations are controlled so as to prevent a location at which rays are focused in a best condition from being shifted by narrowing the aperture of said stop means.

12. An optical system comprising: a stop means having an aperture variable in a shape or a size thereof and a lens system; wherein an optical element producing positive spherical aberration is disposed at a location of a pupil of said optical system or a location conjugate with the pupil of said optical system or in the vicinity thereof.

13. An optical system for endoscopes according to claim 12 wherein the positive spherical aberration produced by said optical element is controlled so as to cancel spherical aberration produced by said relay lens system.

14. An optical system for endoscopes according to claim 12 wherein the positive spherical aberration produced by said optical element is controlled so as to make more remarkable spherical aberration produced by said relay lens system.

15. An optical system for endoscopes according to claim 12 wherein said optical element producing the positive spherical aberration includes a first optical means for producing spherical aberration controlled so as to cancel spherical aberration produced by said relay lens system and a second optical means for producing a second positive spherical aberration.

16. An optical system for endoscopes comprising: a non-flexible endoscope comprising a relay lens system for transmitting an image of an object, and an imaging optical system for imaging an image transmitted by said relay lens system; wherein a stop means having an aperture variable in a shape or a size thereof is disposed in an optical path of said optical system, and wherein an optical element producing positive spherical aberration is disposed at a location of a pupil of said optical system or at a location conjugate with the pupil of said optical system or in the vicinity thereof.

17. An optical system for endoscopes according to claim 16 wherein the positive spherical aberration produced by said optical element is controlled so as to cancel spherical aberration produced by said relay lens system.

18. An optical system for endoscopes according to claim 16 wherein the positive spherical aberration produced by said optical element is controlled so as to make more remarkable spherical aberration produced by said relay lens system.

19. An optical system for endoscopes according to claim 16 wherein said optical element producing the positive spherical aberration includes a first optical means for producing spherical aberration controlled so as to cancel spherical aberration produced by said relay lens system and a second optical means for producing a second positive spherical aberration.

20. An optical system according to any one of claims 1, 2, 3, 4, 5, 9, 10, 11, 12, 16, 13, 17, 14, 18, 15 and 19 wherein the aperture of said stop means is varied dependently on a variation of illuminance on an image surface caused in conjunction with a variation of a distance as measured from said optical system to an object to be observed.

21. An optical system according to any one of claims 1, 2, 3, 4, 5, 9, 10, 11, 12, 16, 13, 17, 14, 18, 15 and 19 wherein said optical system comprises an aspherical surface which has a shape expressed by the formula shown below and satisfies the following condition:

$$E \cdot F < 0$$

$$Sag = (h^2/r)\sqrt{1 + (1 - p(h/r)^2)} + Eh^4 + Fh^6 + \ldots$$

wherein the reference symbol h represents a height of a ray passing through the aspherical surface, the reference symbol Sag designates a value, in a direction along an optical axis on a coordinates system, of a point at a height of h on the aspherical surface (on an assumption that Sag has a value of 0 when h is equal to 0), the reference symbol r designates a radius of curvature on a portion of the aspherical surface located on the optical axis (a radius of curvature on a reference sphere of the aspherical surface), and the reference symbols p, E, F, . . . denote aspherical surface coefficients.

22. An optical system according to any one of claims 13, 17, 14, 18, 15, or 19 wherein said optical element producing the positive spherical aberration is a lens component having a paraxial radius of curvature of substantially zero.

23. An optical system according to any one of claims 13, 17, 14, 18, 15, or 19 wherein said optical element producing the positive spherical aberration is a lens component which has an aspherical surface satisfying the following condition:

$$Mh'' < 5.21 \times 10^{-3}$$

wherein the reference symbol M represents an aspherical surface coefficient of the m'th order and the reference symbol h designates a height of a marginal ray incident on the lens component and the aspherical surface has a shape expressed by the following formula:

$$Sag = (h^2/r)/\sqrt{1+(1-p(h/r)^2)} + Eh^4 + Fh^4 + \ldots$$

24. An optical system according to claim 19 wherein said optical element producing the positive spherical aberration is a lens component which has an aspherical surface satisfying the following condition:

$$Mh^m < 5.21 \times 10^{-3}$$

wherein the reference symbol M represents an aspherical surface coefficient of the m'th order and the reference symbol h designates a height of a marginal ray incident on the lens component and the aspherical surface has a shape expressed by the following formula:

$$Sag = (h^2/r)/\sqrt{1+(1-p(h/r)^2)} + Eh^4 + Fh^4 + \ldots$$

* * * * *